United States Patent
Landesman et al.

(10) Patent No.: US 11,583,177 B2
(45) Date of Patent: Feb. 21, 2023

(54) OPTICAL PROBE FOR CERVICAL EXAMINATION

(71) Applicant: BIOP—MEDICAL LTD., Ramat Gan (IL)

(72) Inventors: Ilan Landesman, Ramat-Gan (IL); Tania Kosoburd, Lod (IL); Oz Seadia, Bat Yam (IL); Shiri Gordon, Tel Aviv (IL)

(73) Assignee: BIOP—MEDICAL LTD., Ramat Gan (IL)

( * ) Notice: Subject to any disclaimer, the term of this patent is extended or adjusted under 35 U.S.C. 154(b) by 213 days.

(21) Appl. No.: 16/636,990

(22) PCT Filed: Aug. 6, 2018

(86) PCT No.: PCT/IL2018/050865
§ 371 (c)(1),
(2) Date: Feb. 6, 2020

(87) PCT Pub. No.: WO2019/030749
PCT Pub. Date: Feb. 14, 2019

(65) Prior Publication Data
US 2021/0007596 A1    Jan. 14, 2021

Related U.S. Application Data

(60) Provisional application No. 62/541,718, filed on Aug. 6, 2017.

(51) Int. Cl.
*A61B 1/303* (2006.01)
*G16H 30/20* (2018.01)
(Continued)

(52) U.S. Cl.
CPC .......... *A61B 1/303* (2013.01); *A61B 1/00006* (2013.01); *A61B 1/00009* (2013.01);
(Continued)

(58) Field of Classification Search
CPC . A61B 1/303; A61B 1/00006; A61B 1/00009; A61B 1/00032; A61B 1/00045;
(Continued)

(56) References Cited

U.S. PATENT DOCUMENTS 5,251,613 A   10/1993  Adair
5,623,932 A   4/1997   Ramanujam et al.
(Continued)

FOREIGN PATENT DOCUMENTS

WO   WO 2008144515 A1 * 11/2008 ......... A61B 1/00101
WO   WO2009009414    * 1/2009  ........... A61B 5/0086
(Continued)

OTHER PUBLICATIONS

Zheng, Wenli, Hyperspeclral wide gap second derivative analysis for in vivo detection of cervical intraepithelial neoplasia, Journal of Biomedical Optics, Journal of Biomedical Optics 20(12), 121303-1-121303-10 Dec. 2015, China.
(Continued)

*Primary Examiner* — Michael J Carey
*Assistant Examiner* — Julianna J Nicolaus
(74) *Attorney, Agent, or Firm* — The Roy Gross Law Firm, LLC; Roy Gross

(57) ABSTRACT

A system for imaging and examination of a cervix, comprising a control module connectable with a changeable head configured to image the cervix and collect a tissue biopsy, the head selected from a group consisting of a digital colposcope module, a transvaginal optical probe module and an endo-cervical endoscope module.
The system may additionally comprise light source(s) to illuminate cervix tissue; sensing device(s) to generate signal (s) from light and/or to acquire image(s) of a portion of a cervix; and processor(s) in communication with the sensing device(s). The system is configured to: (i) analyze the
(Continued)

signal(s); (ii) detect the size of the cervix; (iii) determine parameters defining properties of the cervix; (iv) determine and distinguish normal tissue from abnormal tissue within the cervix; (v) determine the location of area(s) of abnormal tissue in the cervix; and (vi) generate a panoramic view of the cervix.

25 Claims, 17 Drawing Sheets

(51) Int. Cl.
*G16H 50/30* (2018.01)
*G16H 50/20* (2018.01)
*G16H 30/40* (2018.01)
*G16H 40/63* (2018.01)
*G06N 20/00* (2019.01)
*A61B 1/00* (2006.01)
*A61B 1/04* (2006.01)
*A61B 1/06* (2006.01)
*A61B 1/07* (2006.01)
*A61B 5/00* (2006.01)

(52) U.S. Cl.
CPC ...... *A61B 1/00032* (2013.01); *A61B 1/00045* (2013.01); *A61B 1/00105* (2013.01); *A61B 1/00142* (2013.01); *A61B 1/042* (2013.01); *A61B 1/043* (2013.01); *A61B 1/063* (2013.01); *A61B 1/0638* (2013.01); *A61B 1/07* (2013.01); *G06N 20/00* (2019.01); *G16H 30/20* (2018.01); *G16H 30/40* (2018.01); *G16H 40/63* (2018.01); *G16H 50/20* (2018.01); *G16H 50/30* (2018.01); *A61B 5/0071* (2013.01); *A61B 5/0086* (2013.01)

(58) Field of Classification Search
CPC . A61B 1/00105; A61B 1/00142; A61B 1/042; A61B 1/043; A61B 1/063; A61B 1/0638; A61B 1/07; A61B 5/0071; A61B 5/0086; G06N 20/00; G16H 30/20; G16H 30/40; G16H 40/63; G16H 50/20; G16H 50/30
See application file for complete search history.

(56) References Cited

U.S. PATENT DOCUMENTS

| | | | |
|---|---|---|---|
| 5,986,271 A | 11/1999 | Lazarev et al. | |
| 6,590,651 B1 | 7/2003 | Bambot et al. | |
| 6,847,490 B1* | 1/2005 | Nordstrom | A61B 1/00142 359/642 |
| 7,127,282 B2 | 10/2006 | Nordstrom et al. | |
| 8,005,527 B2 | 8/2011 | Zelenchuk | |
| 8,320,650 B2 | 11/2012 | Demos et al. | |
| 8,380,268 B2 | 2/2013 | Georgakoudi et al. | |
| 9,495,745 B2* | 11/2016 | Remiszewski | G06T 7/33 |
| 2003/0013973 A1 | 1/2003 | Georgakoudi et al. | |
| 2007/0213590 A1 | 9/2007 | Squicciarini | |
| 2007/0232874 A1 | 10/2007 | Ince | |
| 2008/0194969 A1 | 8/2008 | Werahera et al. | |
| 2012/0232404 A1 | 9/2012 | Bambot et al. | |
| 2016/0287063 A1 | 10/2016 | Ramanujam et al. | |

FOREIGN PATENT DOCUMENTS

| | | | |
|---|---|---|---|
| WO | 2009029254 A1 | 3/2009 | |
| WO | 2011066149 A1 | 6/2011 | |
| WO | 2014007759 A1 | 1/2014 | |
| WO | 2015040570 A1 | 3/2015 | |
| WO | 2015173676 A2 | 11/2015 | |

OTHER PUBLICATIONS

PCT International Searching Authority for International Application No. PCT/IL2018/050865, dated Nov. 29, 2018, 1pp.
Liu, Xuan, Dark-field illuminated reflectance fiber bundle endoscopic microscope, Journal of Biomedical Optics, 16(4), Apr. 2011, Baltimore, Maryland.
PCT Search Report for International Application No. PCT/IL2018/050865, dated Nov. 29, 2018, 1pp.
Collier, Tom, Sources of scattering in cervical tissue: determination of the scattering coefficient by confocal microscopy, Applied Optics, vol. 44, No. 11, Apr. 10, 2005, 2072-2081.
Hunter, Martin, Tissue Self-Affinity and Polarized Light Scattering in the Born Approximation: A New Model for Precancer Detection, Physical Review Letters, 138102-1-138102-4.
PCT Written Opinion of the International Searching Authority for International Application No. PCT/IL2018/050865, dated Nov. 29, 2018, 7pp.
Yu Bing, Emerging Optical Techniques for Detection of Oral, Cervical and Anal Cancer in Low-Resource Settings, Austin Journal of Biomedical Engineering, vol. 1, Issue 1, 2014 pp. 1-15.
Tan. New technologies and advances in Colposcopic assessment. Best practices and research clinical obstetrics and gynecology. 25, 2011: p. 667-677, Australia.
Dong, Jint-Tao, Optical design of color light-emitting diode ring light for machine vision inspection, Optical Engineering, Apr. 2011/vol. 50(4).
Spackman, Wade R, Adjunctive colposcopy technologies for examination of the uterine cervix—DySIS, LuViva Advanced Cervical Scan and Niris Imaging System: a systematic review and economic evaluation, Health Technology Assessment, 1-260pp, vol. 17, Issue 8, Mar. 2013, UK.
Tidy, JA, Accuracy of detection of high-grade cervical intraepithelial neoplasia using electrical impedance spectroscopy with colposcopy, Gynaecological Oncology, 400-411pp, Mar. 2013, UK.
Bekkers, Rudd L Does experience in colposcopy improve identification, European Journal of Obstetrics and Gynecology and Reproductive Biology, Nov. 2008, p. 75-78, vol. 141, Issue 1.
PCT Extended European Search Report for International Application No. PCT/IL201805086E, dated Jun. 24, 2020, 7pp.
Hunter, Martin, Tissue Self-Affinity and Polarized Light Scattering in the Born Approximation: A New Model for Precancer Detection, Physical Review Letters, 138102-1—138102-4 (2006).

* cited by examiner

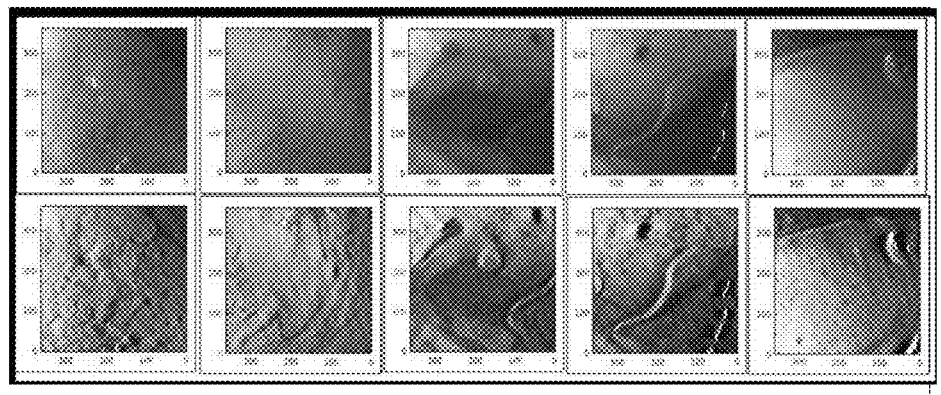
Fig. 20A
Fig. 20B
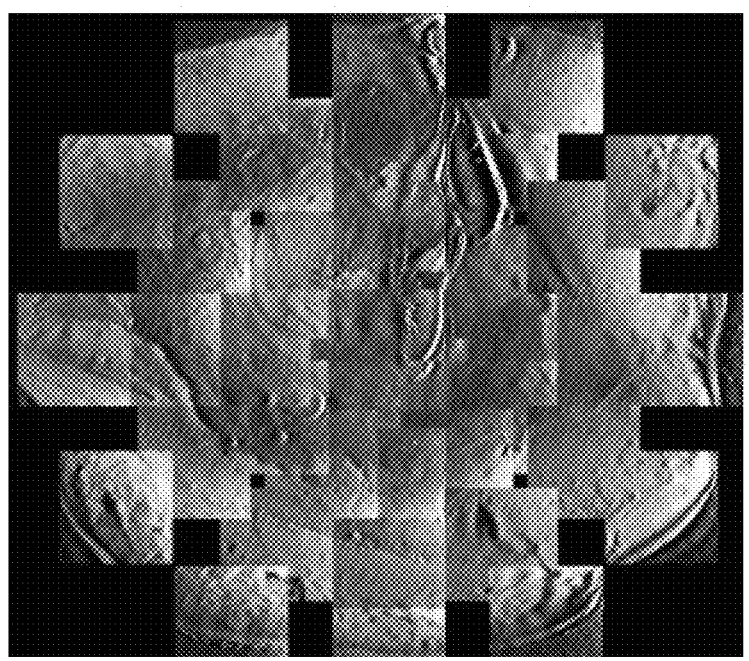
Fig. 21

OPTICAL PROBE FOR CERVICAL EXAMINATION

CROSS REFERENCE TO RELATED APPLICATIONS

This application is a National Phase of PCT Patent Application No. PCT/IL2018/050865 having International filing date of Aug. 6, 2018, which claims the benefit of priority of U.S. Provisional Application No. 62/541,718 filed on Aug. 6, 2017 entitled OPTICAL PROBE FOR CERVICAL EXAMINATION. The contents of the above applications are all incorporated by reference as if fully set forth herein in their entirety.

FIELD OF THE INVENTION

The present invention generally pertains to a system and method for providing an optical probe for cervical examination.

BACKGROUND OF THE INVENTION

Cervical cancer is one of the most common neoplasms of the female genital tract. It is the second-leading cause of cancer death among women in developing countries and the fourth cause of cancer-associated death worldwide. Early diagnosis of abnormal cells in the cervix prevents their development into cervical cancer and thus reduces morbidity and mortality.

The uterine cervix is easily screened for several reasons. First, the tumoral changes occur in a specific area, called the transitional zone, around the "external os" (opening of the cervical canal into the vagina). Second, these are slow growing tumors. Third, this area is external to the body and can be easily observed by a gynecologist.

One common screening method, the Pap test, has been in use for decades. During a Pap test, a large number of cells, obtained by scraping the cervical epithelium, are smeared onto a slide or into a tube of liquid, and are then fixed and stained for cytological examination. Unfortunately, the Pap test is unable to achieve a concurrently high sensitivity and high specificity due to both sampling and analysis errors. Estimations of the sensitivity and specificity of the Pap test range from 11-99% and 14-97%, respectively, where the term sensitivity is defined as the percentage correct in classification of pre-cancerous tissue samples and the term specificity is defined as the percentage correct in classification of normal tissue samples.

According to the National Cancer Institute (NCI), about 55 million Pap tests are performed each year in the USA. Of these, approximately 3.5 million have results defined as "abnormal" and require medical follow-up. On follow-up, most of the "abnormal" tests are found to be false positives, where the test falsely indicated the presence of cervical intraepithelial neoplasia (CIN) 2, 3 or invasive cancer.

Additionally, analyzing Pap tests is extremely labor intensive and requires highly trained professionals. A patient with an abnormal Pap test indicating the presence of CIN or invasive cancer needs to then undergo a colposcopic examination to locate abnormal epithelium, and, if needed, undergo a biopsy in the areas indicated by the colposcopic examination, followed by histological confirmation of the clinical diagnosis.

A colposcopic examination involves the systematic evaluation of the lower genital tract including the uterine cervix, with particular emphasis on the superficial epithelium and blood vessels of the underlying stroma. Colposcopic testing is a subjective exam and suffers from the following limitations:

Non-standardized, variable procedure
Subjective, unquantified ace to whitening observations
Accurate identification of optimal biopsy sites can be challenging
Monitoring longitudinal changes is difficult The examination should be performed by trained personnel in order to ensure an optimum procedure. If abnormal areas are found, biopsies will be taken from such areas; if no obviously abnormal areas are identified, the clinician may randomly take biopsies from the four quadrants of the cervix. Biopsies may cause discomfort and bleeding to the patient, as well as anxiety. Biopsy results are typically provided within 3 weeks.

When performed according to acceptable protocols and assessment methods, colposcopy is traditionally viewed as an accurate diagnostic tool. However, a meta-analysis of nine studies published has estimated the sensitivity and specificity of colposcopy as being 96% and 48%, respectively, for differentiating between normal and abnormal tissue (Wade et al. 2009. Adjunctive colposcopy technologies for examination of the uterine cervix—DySIS, LuViva Advanced Cervical Scan and Niris Imaging System: a systematic review and economic evaluation. Health Technology Assessment 17(8):1-260). In addition, experience does not appear to improve the performance of colposcopists (Bekkers et al. 2008. *Does experience in colposcopy improve identification of high grade abnormalities?* Eur J Obstet Reprod Biol 141: 75-78).

In recent years, a number of new technologies have been introduced to advance the practice of colposcopy. Although none have gained widespread clinical use, spectroscopic devices appear to offer the highest level of sensitivity (Tan et al. 2011. New technologies and advances in Colposcopic assessment. Best practices and research clinical obstetrics and gynecology. 25: 667-677).

Light scattering spectroscopy (LSS), is a technique in which the angular and wavelength dependence of elastically scattered light is used to infer the spatial frequency spectrum of a scattering object. Oncogenic transformation of the tissue leads also to morphological and biochemical changes in spectral distribution and angular distribution of the light scattered by the tissue. LSS has been shown to be useful in detecting pre-cancerous tissue (Hunter et al. 2006. *Tissue self-affinity and polarized light scattering in the Born approximation: A new model for pre-cancer detection.* PRL 97: 138102-1-138102-4 and Collier et al. 2005. Sources of scattering in cervical tissue: determination of the scattering coefficient by confocal microscopy. Applied Optics. 44(11): 2072-2081).

Preliminary clinical studies have shown the clinical feasibility of using spectrum analysis in cervical tissue differentiation for detection of cervical intraepithelial neoplasia (Zheng et al. 2015. Hyperspectral wide gap second derivative analysis for in vivo detection of cervical intraepithelial neoplasia. Journal of Biomedical Optics. 20(12): 121303-1 121303-10).

Patient movement during examination can lead to inaccurate determination of the location of abnormal tissue, which can lead to inaccurate biopsy location and, therefore, false negatives during diagnosis.

There are several instruments developed in the last few years which increase the sensitivity and specificity of diagnostic results of colposcopy. A majority of the devices combine results acquired using different optical effects for diagnosis, with the number of optical effects used depending on the device. Combining results leads to a higher diagnostic accuracy than would be possible with a single method.

The prior art discloses local probes used as an addition to a colposcope, which are configured for manual screening and cannot provide a map with the exact locations of suspicious areas (see U.S. Pat. Nos. 8,380,268, 8,320,650, 8,005,527, US Patent publication no. US2008/0194969, US patent publication no. US2003/0013973, PCT Publication no. WO2014/007759 and J. A. Tidy et al., *Accuracy of detection of high-grade cervical intraepithelial neoplasia using electrical impedance spectroscopy with colposcopy. BJOG: An International Journal of Obstetrics & Gynaecology*, 120, No. 4, pp. 400-411, March 2013).

For example, U.S. Pat. No. 8,005,527 discloses a system and method for in situ discrimination between healthy and diseased tissue. A fiber optic based probe is employed to direct ultraviolet illumination onto a tissue specimen and to collect the fluorescent response radiation. The response radiation is observed at three selected wavelengths, one of which corresponds to an isosbestic point. In one example, the isosbestic point occurs at about 431 nm. The intensities of the observed signals are normalized using the 431 nm intensity. A score is determined using the ratios in a discriminant analysis. The tissue under examination is resected or not, based on the diagnosis of disease or health, according to the outcome of the discriminant analysis.

U.S. Pat. No. 6,590,651 discloses an apparatus and method which utilize a device comprising a limited number of interrogation devices which can carry out a large number of measurements on a target tissue. The plurality of detection devices are arranged in a predetermined pattern on a tissue-contacting face of the instrument. The face of the instrument is located adjacent to the target tissue and a plurality of tissue-characteristic measurement are simultaneously conducted. The detection devices are moved to a new position, preferably without moving the tissue contacting face, and a second plurality of tissue-characteristic measurements are simultaneously conducted. By conducting a series of measurement cycles in this manner, the ultimate resolution of the device is increased, without the need to increase the instrument resolution, which reduces potential cross-talk errors. Further, a plurality of tissue characteristics are simultaneously obtained from locations spaced across the target tissue during each measurement cycle.

US patent publication no. US2012/232404 discloses a method and apparatus that interrogate, receive, and analyze full emission spectra for at least one fluorescence excitation wavelength and for at least one reflectance measurement to determine tissue characteristics and correlate the same to photographic images. Further, the system and method accomplish this measurement rapidly by increasing the light throughput by integrating optics into a hand-held unit, avoiding the need for a coherent fiber optic bundle. The method includes illuminating a first portion of a target tissue with optical energy, forming a first image of the target tissue, illuminating a second portion of the target tissue with optical energy, performing spectroscopic measurements on optical energy reflected and/or emitted by the target tissue upon illumination of the second portion of the target tissue with optical energy, and determining tissue characteristics of the target tissue based on the results of the spectroscopic measurements.

U.S. Pat. No. 7,127,282 discloses a method and a system for discriminating between healthy cervical tissue and pathologic cervical tissue based on the fluorescence response of the tissue to laser excitation (LIF) and the backscatter response to illumination by white light (in the spectral range of 360 to 750 nm). Combining LIF and white light responses, as well as evaluating a spatial correlation between proximate cervical tissue sites in conjunction with a statistically significant "distance" algorithm, such as the Mahalanobis distance between data sets, can improve the discrimination between normal and abnormal tissue. The results may be displayed in the form of a map of the cervix representing the suspected pathology.

None of the abovementioned prior art documents teach use of a colposcope.

U.S. Pat. No. 5,623,932 discloses an apparatus and methods to distinguish in vivo normal and abnormal cervical tissue and to detect cervical intraepithelial neoplasia (CIN) in a diagnostic cervical tissue sample. Induced fluorescence intensity spectra from known normal cervical tissue and a diagnostic tissue sample are obtained from the same patient. Peak fluorescence intensity values for normal tissue samples are averaged, as are slope measurements from predetermined portions of spectra induced in both normal cervical tissue and the diagnostic tissue sample. Peak fluorescence intensities of diagnostic tissue spectra are divided by average peak fluorescence intensity values for normal tissue in the same patient to yield relative peak fluorescence intensity values. Normal and abnormal cervical tissues are distinguished using a predetermined empirical discriminant function of slope measurements derived from normal tissue spectra and relative peak fluorescence intensity measurements in the same patient. CIN is distinguished from tissue with human papilloma virus infection or inflammation using a predetermined empirical discriminant function of average slope measurements on spectra from known normal tissue and slope measurements on a diagnostic tissue spectrum.

Therefore, there is a long-felt need for an instrument that can differentiate between normal and abnormal tissues and provide a map of normal and of abnormal tissue areas in a scanned region, which does not require highly-skilled personnel to interpret the results, does not require a long interval between testing and diagnosis, and does not provide inaccurate results if a patient moves during testing.

SUMMARY OF THE INVENTION

It is an object of the present invention to disclose a system for providing an optical probe for cervical examination.

It is another object of the present invention to disclose a system for imaging a cervix, comprising:
  at least one control module; and
  at least one changeable head module, at least partially reversibly connectable to said control module; configured to image at least a portion of said cervix;
  wherein, on connection, said control module is configured to provide at least one member of a group consisting of activation and movement to said at least one changeable head module;
  further wherein, upon connection between said control module and said at least one changeable head module, a cervical examination device is provided.

It is another object of the present invention to disclose a system for imaging a cervix, comprising:
  at least one light source configured to generate light to illuminate tissue in at east one portion of said cervix;
  at least one sensing device configured to generate at least one signal from light impinging on said at least one sensing device; and at least one processor in communication with said at least one sensing device, said at least one processor configured to analyze each said at least one signal;

wherein, said at least one processor is configured to:

(i) determine at least two substantially different parameters, each of which defines at least one property of said cervix;

(ii) analyze said at least one signal, based on said at least two parameters, to determine and distinguish normal tissue from abnormal tissue within said cervix.

It is another object of the present invention to disclose a system for imaging a cervix, comprising:

at least one first sensing device configured to provide at least one first image at a first resolution of a first at least a portion of a cervix;

at least one second sensing device configured to provide at least one second image at a second resolution of a second at least a portion of a cervix; said at least one first image and said at least one second image at least partially overlap;

said second resolution being higher than said first resolution; and, a processor in communication with said at least one first sensing device and said at least one second sensing device, configured to image process said at least one first image and said at least one second image to generate a combined image;

wherein said combined image is a panoramic view of at least a portion of said cervix.

It is another object of the present invention to disclose a device for imaging a cervix, comprising:

at least one light source, configured to generate light, said light illuminating tissue in at least a portion of said cervix; and at least one sensing device being positioned at a distance $D_s$ from said at least one light source, said at least one sensing device is configured to generate at least one signal from at least a portion of light scattered from said illuminated tissue;

wherein, for said distance $D_s$, in use, said at least one sensing device senses only light scattered from said tissue.

It is another object of the present invention to disclose a device for imaging a cervix, comprising: at least one laser configured to generate laser light, said laser configured to illuminate with said laser light at least a portion of said cervix;

at least one sensing device configured to acquire at least one image of said at least a portion of a cervix; said at least one sensing device is positioned relative to said at least one laser so as to prevent said laser light from passing directly from said at least one laser to said at least one sensing device;

a beam of said laser light is parallel to and at a predetermined distance from a centerline of said at least one sensing device; and at least one processor in communication with said at least one sensing device, said at least one processor configured to measure, from said at least one image, a distance between said at least one image of at least a portion of said cervix and a centerline of said at least one image, said distance between said at least one image of at least a portion of said cervix and said centerline of said at least one image being a spot distance;

wherein, from a ratio of said spot distance and said predetermined distance a size of said at least a portion of said cervix is automatically detectable.

It is another object of the present invention to disclose a device for imaging a cervix comprising:

at least one camera configured to acquire at east one image of at least a portion of a cervix;

at least one sensing device configured to generate at least one signal from light impinging on said at least one sensing device; and at least one processor in communication with said at least one sensing device, said at least one processor configured to analyze said at least one signal, determine at least one parameter which defines at least one property of said cervix, analyze said at least one parameter to define and distinguish normal tissue and abnormal tissue within said cervix as a function of location within said cervix and, if there exists at least one area of abnormal tissue, to determine a location in said cervix of said at least one area of abnormal tissue;

wherein said at least one processor is further configured, if there exists said at least one area of abnormal tissue, to mark at said location on said image said at least one area of said abnormal tissue.

It is another object of the present invention to disclose a device for imaging a cervix comprising:

at least one camera configured to acquire: least one image of at least a portion of a cervix;

at least one sensing device configured to generate at least one signal from light impinging on said at least one sensing device; and at least one processor in communication with said at least one sensing device, said at least one processor configured to analyze said at least one signal, determine at least one parameter which defines at least one property of said cervix, analyze said at least one parameter to determine probability of normal tissue and abnormal tissue within said cervix as a function of location within said cervix, and overlay on said at least one image said probability of normal tissue and abnormal tissue within said cervix as a function of location within said cervix;

wherein said at least one processor is further configured to generate a map indicating the probability of normal tissue and abnormal tissue as a function of location in said at least one image of at least a portion of a cervix.

It is another object of the present invention to disclose a method for imaging a cervix comprising steps of:

providing a system for imaging a cervix comprising:
at least one control module; and
at least one changeable head module, at least partially reversibly connectable to said at least one control module; configured to image at least a portion of said cervix;

providing a cervical examination device by connecting said at least one changeable head module to said at least one control module; and at least one member of a group consisting of activating and moving said at least one changeable head module via controls on said at least one control module.

It is another object of the present invention to disclose a method for imaging a cervix comprising steps of:

providing a system for imaging a cervix comprising:
at least one light source configured to generate light to illuminate tissue in at least one portion of said cervix;

at least one sensing device configured to generate at least one signal from light impinging on said at least one sensing device; and at least one processor in communication with said at least one sensing device, said at least one processor configured to analyze each said at least one signal;

illuminating said tissue, thereby scattering light from said tissue and impinging at least a portion of said scattered light onto said at least one sensing device;

generating said at least one signal from said at least a portion of said scattered light;

determining at least two substantially different parameters, each of which defines at least one property of said cervix; and for each said at least one sensing device, analyzing said at least one signal;

thereby determining and distinguishing normal tissue from abnormal tissue within said cervix.

It is another object of the present invention to disclose a method for imaging a cervix comprising steps of:

providing a system for imaging a cervix comprising:

at least one first sensing device configured to provide at east one first image at a first resolution of a first at least a portion of a cervix;

at least one second sensing device configured to provide at least one second image at a second resolution of a second at least a portion of a cervix; said at least one first image and said at least one second image at least partially overlap;

said second resolution being higher than said first resolution; and at least one processor in communication with said at least one first sensing device and said at least one second sensing device, configured to image process said at least one first image and said at least one second image to generate a combined image;

acquiring said at least one first image at said first resolution of said first at least a portion of a cervix;

acquiring said at least one second image at said second resolution of said second at least a portion of a cervix;

image processing said at least one first image and said at least one second image; and stitching together said at least one first image and said at least one second image, thereby generating a combined image;

wherein said combined image is a panoramic view of at least a portion of said cervix.

It is another object of the present invention to disclose a method for aging a cervix comprising steps of:

providing a device for imaging a cervix comprising:

at least one light source, configured to generate light, said light illuminating tissue in at least a portion of said cervix; and at least one sensing device being positioned at a distance $D_s$ from said at least one light source, said at least one sensing device is configured to generate at least one signal from at least a portion of light scattered from said illuminated tissue;

selecting said distance $D_s$ so that, in use, said at least one sensing device senses only light scattered from said tissue;

illuminating said tissue;

thereby generating scattered light from said tissue; and detecting at least a portion of said scattered light by at least one sensing device;

wherein said sensed light comprises only light scattered from said cervix.

It is another object of the present invention to disclose a method for imaging a cervix comprising steps of:

providing a device for imaging a cervix, comprising:

at least one laser configured to generate laser light, said laser configured to illuminate with said laser light at least a portion of a cervix;

at least one sensing device configured to acquire at least one image of said at least a portion of a cervix; said at least one sensing device is positioned relative to said at least one laser so as to prevent said laser light from passing directly from said at least one laser to said at least one sensing device;

a beam of said laser light is parallel to and at a predetermined distance from a centerline of said at least one sensing device; and at least one processor in communication with said at least one sensing device, said at least one processor configured to measure, from said at least one image, a distance between said at least one image of at least a portion of said cervix and a centerline of said at least one sensing device, said distance between said at least one image of at least a portion of said cervix and said centerline of said at least one sensing device being a spot distance;

generating said laser light;

acquiring said at least one image of said laser light;

measuring said spot distance;

automatically detecting a size of said at least a portion f said cervix from a ratio of said spot distance and said predetermined distance.

It is another object of the present invention to disclose a method for imaging a cervix comprising steps of:

providing a device for imaging a cervix comprising:

at least one camera configured to acquire at least one image of at least a portion of a cervix;

at least one sensing device configured to generate at least one signal from light impinging on said at least one sensing device; and at least one processor in communication with said at least one sensing device, said at least one processor configured to analyze said at least one signal, determine at least one parameter which defines at least one property of said cervix, analyze said at least one parameter to define and distinguish normal tissue and abnormal tissue within said cervix as a function of location within said cervix and, if there exists at least one area of abnormal tissue, to determine a location in said cervix of said at least one area of abnormal tissue;

acquiring said at least one image of at least a portion of a cervix;

determining said at least one parameter which defines said at least one property of said cervix;

analyzing said at least one signal;

defining and distinguishing said normal tissue and said abnormal tissue said cervix as a function of location within said cervix;

determining said location in said cervix of said at least one area of abnormal tissue; and marking on said at least one image of at least a portion of a cervix, said at least one area of said abnormal tissue.

It is finally an object of the present invention to disclose a method for imaging a cervix comprising steps of:

providing a device for imaging a cervix comprising:

at least one camera configured to acquire at least one image of at least a portion of a cervix;

at least one sensing device configured to generate at least one signal from light impinging on said at least one sensing device; and at least one processor in communication with said at least one sensing device, said at least one processor configured to analyze said at least one signal, determine at least one parameter which defines at least one property of said cervix, analyze said at least one parameter to determine probability of normal tissue and abnormal tissue within said cervix as a function of location within said cervix, and overlay on said at least one image said probability of normal tissue and abnormal tissue within said cervix as a function of location within said cervix;

acquiring said at least one image of at least a portion of a cervix;

generating said at least one signal from said light impinging on said at least one sensing device;

analyzing said at least one signal;

determining said at least one parameter which defines at least one property of said cervix;

analyzing said at least one parameter to determine said probability of normal tissue and abnormal tissue within said cervix as a function of location within said cervix;

overlaying on said at least one image said probability of normal and abnormal tissue within said cervix as a function of location within said cervix;

thereby generating a map indicating the probability of normal tissue and abnormal tissue as a function of location in said at least one image of at least a portion of a cervix.

BRIEF DESCRIPTION OF THE FIGURES

In order to better understand the invention and its implementation in practice, a plurality of embodiments will now be described, by way of non-limiting example only, with reference to the accompanying drawings, wherein

FIG. 20A-B depicts high-resolution images of portions of the cervix. FIG. 20A illustrates the raw images, while FIG. 20B illustrates the images after contrast enhancement and illumination correction;

FIG. 21 depicts a panoramic image of the entire cervical scan with high resolution;

DETAILED DESCRIPTION OF THE PREFERRED EMBODIMENTS

Figure 1:
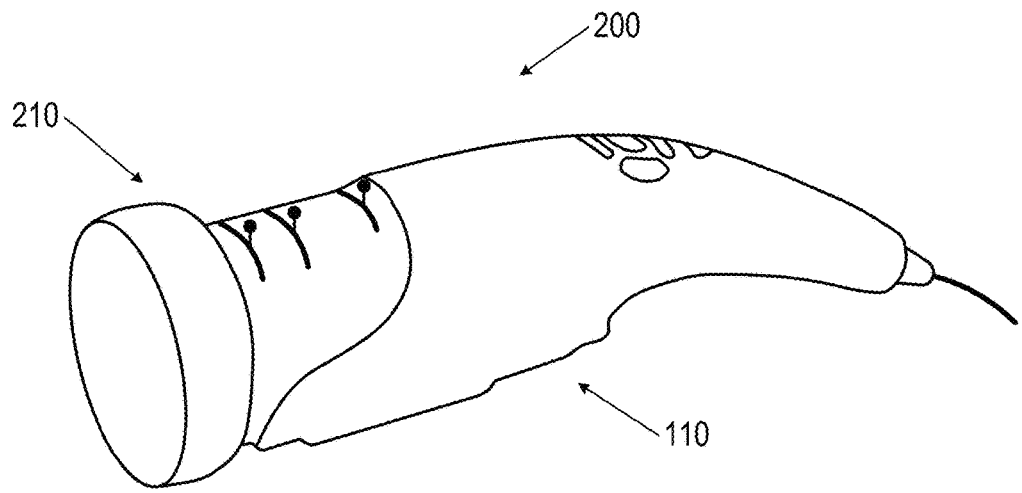
FIG. 1 depicts an embodiment comprising modules configured to provide an external probe (a colposcope)

The following description is provided, alongside all chapters of the present invention, so as to enable any person skilled in the art to make use of said invention and sets forth the best modes contemplated by the inventor of carrying out this invention. Various modifications, however, will remain apparent to those skilled in the art, since the generic principles of the present invention have been defined specifically to provide a means and method for providing a modular device to image the uterine cervix and lower genital tract under illumination and magnification, where the device utilizes different optical phenomena for determining the presence of and location of abnormal cells.

The term 'glass' hereinafter refers to a material transparent at least in the visible and near infrared, used to cover the light sources, sensors and electronics of the modular optical units disclosed herein. The term "glass" can include glass, a transparent polymer, or a transparent mineral such as, but not limited to, diamond, quartz, or colorless amethyst.

The term 'module' hereinafter refers to unit which is reversibly connectable to at least one other unit. Each module is configured for handling and storage as an independent unit and each module is configured for quick and easy connection to and disconnection from at least one other module.

The term 'cervical examination device' hereinafter refers to a device which can carry out an examination of tissue. A cervical examination device is generated by connecting together at least two modules.

The term 'unit' hereinafter refers to a stand-alone portion of the device.

The term 'suspicious area' hereinafter refers to a region in the tissue that has at least a moderate probability of containing precancerous or cancerous cells.

The term 'abnormal tissue' hereinafter refers to tissue comprising precancerous cells, cancerous cells and any combination thereof.

The term 'abnormal cell' hereinafter refers to a cells which is precancerous or cancerous.

The modular optical probe of the present invention typically relies on different optical phenomena, typically three different optical phenomena, to distinguish between normal and abnormal cells at or near the surface of living tissue, typically in the uterine cervix, in the vagina, in tissues adjacent thereunto, and any combination thereof. The collected data are interpreted by software based on machine-learning algorithms.

The output of the modular optical probe can include both high-resolution micro-images of the tissue, and a color map of the tissue, indicating the probability of abnormalities, typically of the epithelium.

In the prior art, the usefulness of colposcopy could be limited by difficulty in identifying areas with possibly abnormal tissue (suspicious areas), and by difficulty in accurately specifying the location of these areas so that there would be a reasonable certainty of removing tissue from a suspicious area during a biopsy. The physician manually positioned the colposcope and observed the image, and, using tissue changes visible to the naked eye, selected the suspicious areas. Precancerous areas can be difficult to distinguish from normal tissue, so suspicious areas could easily be missed. In addition, movement of the patient during a scan, the difficulty in accurately determining the exact size of the cervix and difficulty in ensuring a precise orientation of the colposcope could mean that a biopsy would be taken near, but not in, a suspicious area, thereby missing precancerous or cancerous tissue, leading to a false negative diagnosis.

The Modular System and Descriptions of the Modules

Figure 2:
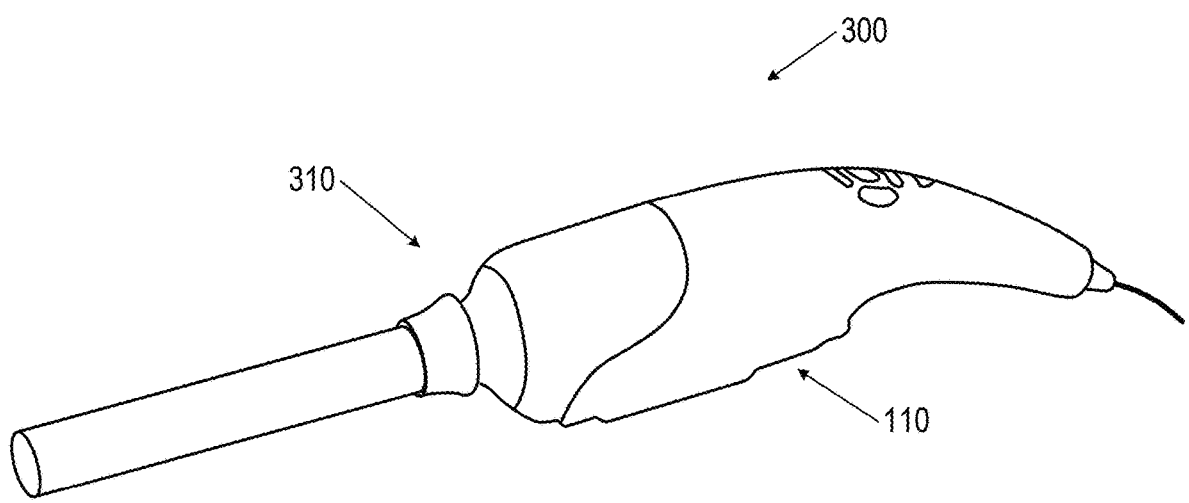
FIG. 2 depicts an embodiment comprising modules configured to be inserted into the vagina (a vaginal optical probe)
Figure 3:
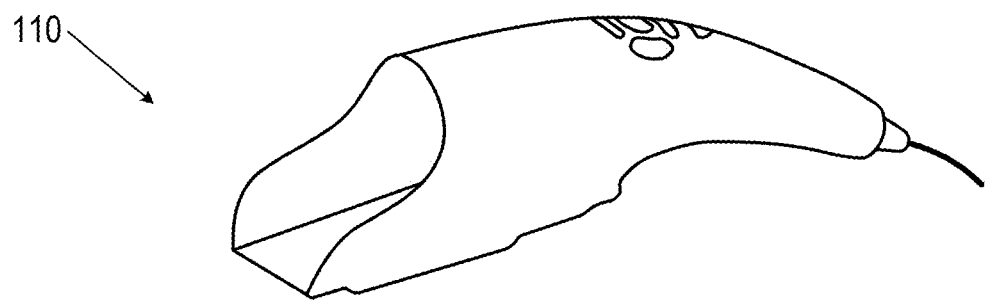
FIG. 3 depicts an embodiment of a control unit.
Figure 4:
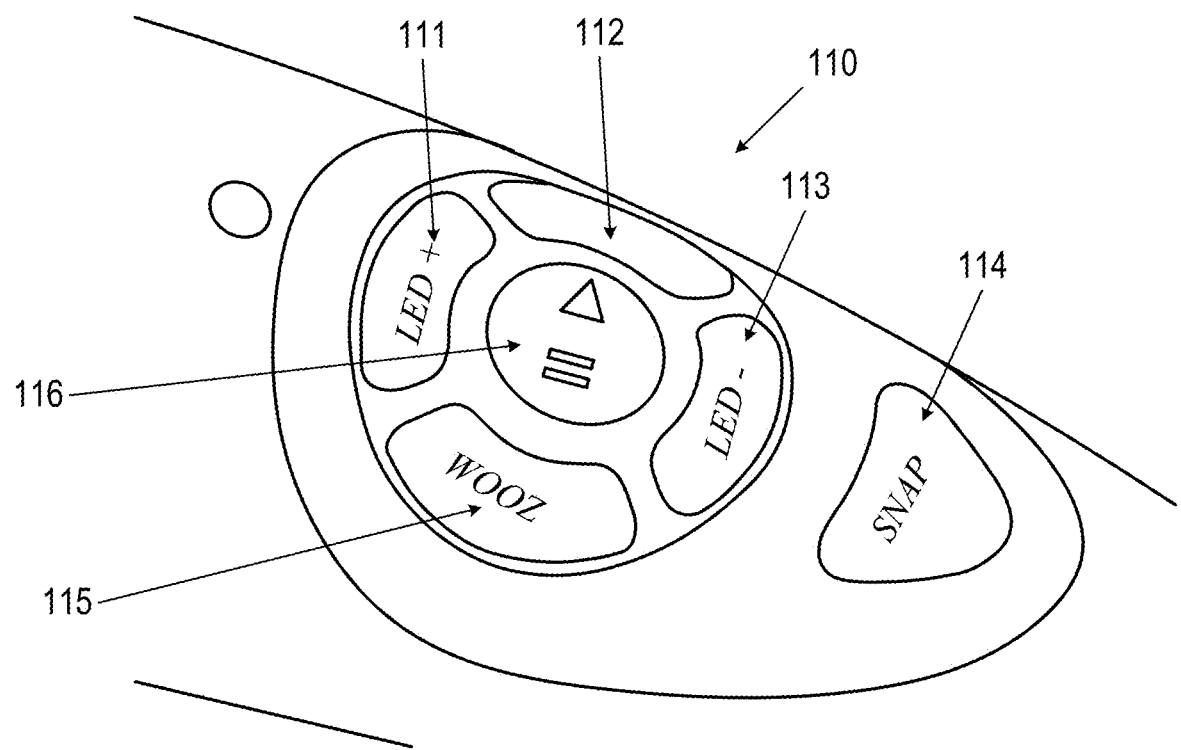
FIG. 4 depicts a close-up of the embodiment of a control unit, showing the controls.
Figure 5:
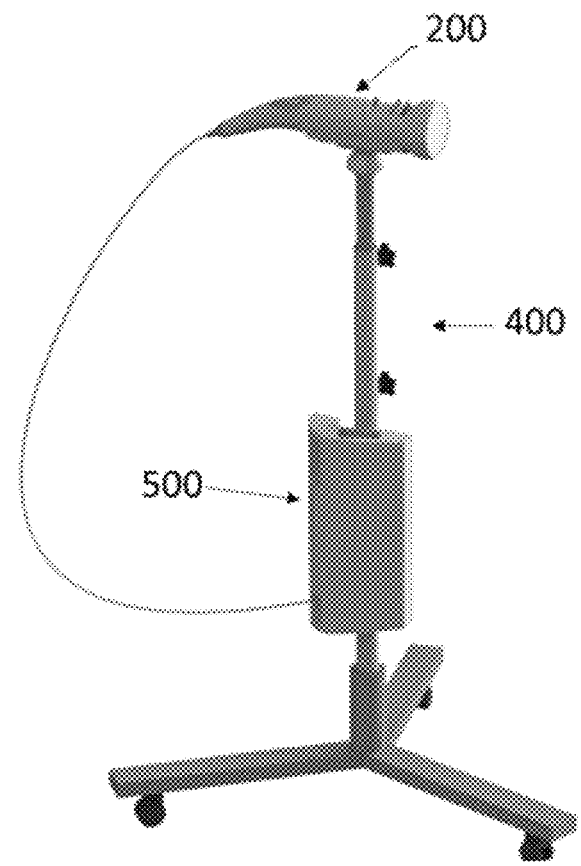
FIGS. 5 and 6 depict an embodiment of a support unit configured to support an assembled device.
Figure 6:
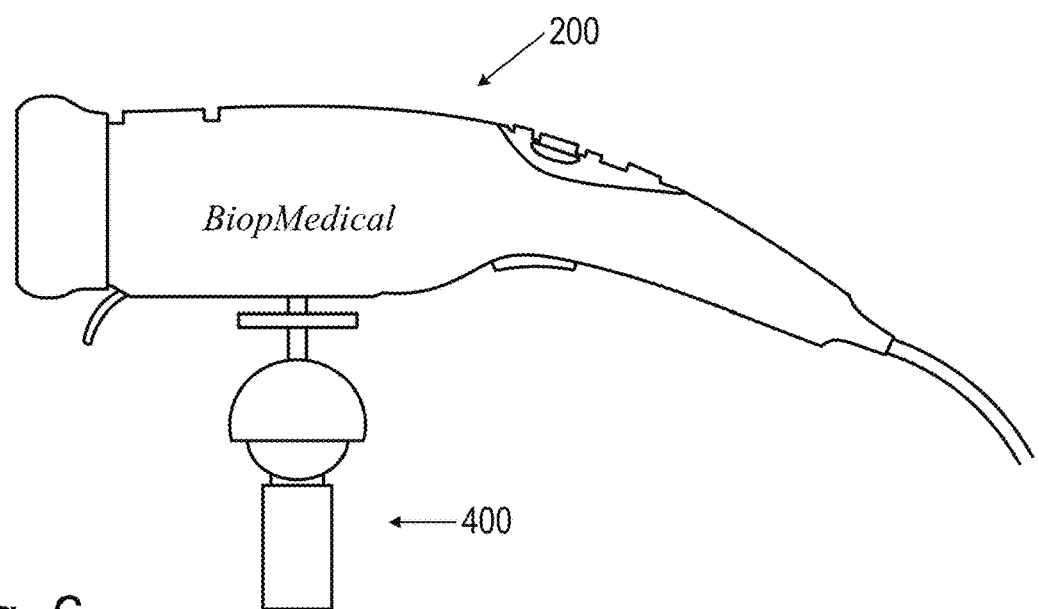
Figure 7A:
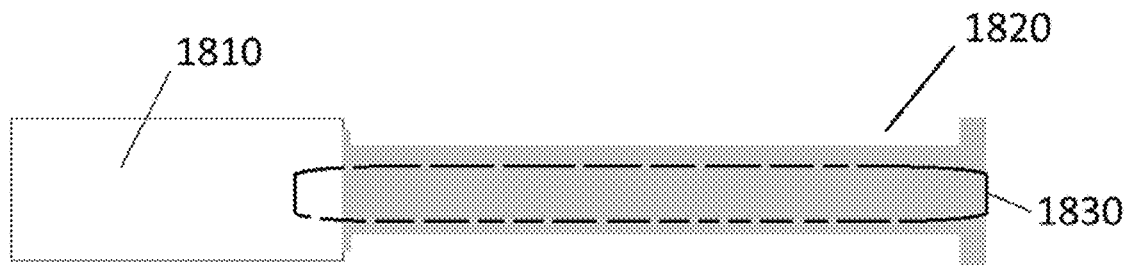
FIG. 7A-B schematically illustrates an embodiment of an endo-cervical endoscope, with FIG. 7A schematically illustrating an external view of an embodiment of an endo-cervical endoscope, and FIG. 7B schematically illustrating an internal view of an endo-cervical endoscope.
Figure 7B:
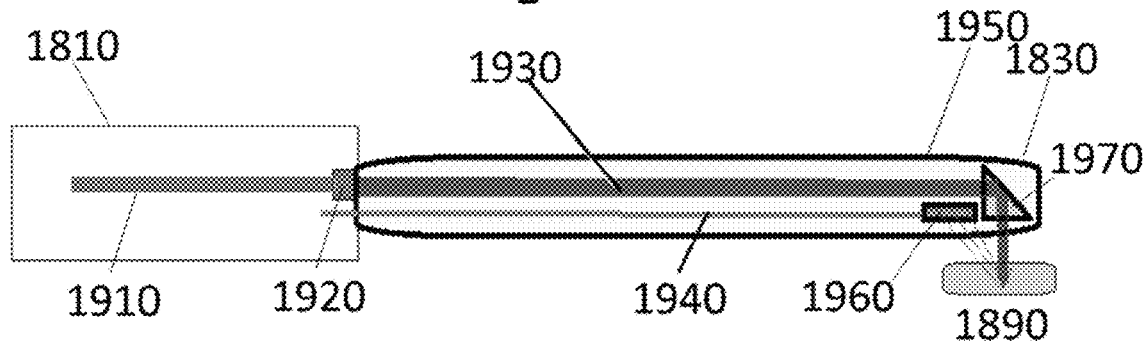

An embodiment of a modular optical probe is shown in FIGS. 1 to 6, with FIG. 1 showing modules (110, 210) configured to provide an external probe (a digital colposcope, 200), FIG. 2 showing modules (110, 310) configured to be inserted into the vagina (a transvaginal optical probe, 300), FIGS. 3 and 4 showing the control unit, and FIGS. 5 and 6 showing a configuration of an accessory, a support unit configured to support a cervical examination device (200, 300) and additionally configured to support a base unit (500).

The digital colposcope (200) offers fully digital and high-resolution imaging of the cervix, from outside the cervix. The field of view can be illuminated by at least one non-coherent light source configured to provide wide-spectrum visible light and a camera or other imaging device can capture color images, preferably presenting magnified images.

The light source, typically one or more LEDs, although any source known in the art can be used, can be a white light source, or multiple sources, such as red, blue, green and other wavelength light sources can be used.

In some embodiments, at least one head module is configured such that a cervical examination device comprising that head module can provide at least one acetic acid wash for the cervix. The acetic acid wash can be provided automatically by the system, by the system when commanded by a user, manually via a passage in the head module, and any combination thereof. In preferred embodiments, the cervical examination device is at least one of digital colposcope and a transvaginal optical probe.

In some embodiments, at least one head module is configured such that at least one tissue biopsy can be collected by it. The tissue biopsy collection can be made automatically by the system, by the system when commanded by a user, manually via a passage in the head module, and any combination thereof. In preferred embodiments, the head module configured to collect a tissue biopsy is selected from a group consisting of a digital colposcope, a transvaginal optical probe, an endo-cervical endoscope module and any combination thereof.

The transvaginal optical probe (300) is insertable into the vagina until it contacts the uterine cervix. It can scan the tissue, preferably automatically, using a plurality of different optical methods and it can provide a 360° view, preferably in color, of the uterine cervix around the external os. In preferred embodiments, a color map overlaid on the 360° view indicates the probability of normal tissue and abnormal tissue as a function of location in the displayed areas. In preferred embodiments, a learning algorithm can be used to improve the quality and accuracy of the results. In some embodiments, the acquired data are analyzed in real time.

The endo-cervical canal endoscope (not shown) is configured to scan the cervical canal, acquire optical data, preferably using a plurality of optical methods, and analyze the acquired data in real time. The endo-cervical canal endoscope comprises an endo-cervical canal endoscope connected to a control unit (110). In preferred embodiments, a learning algorithm can be used to improve the quality and accuracy of the results. In some embodiments, the scan is manually controlled, e.g., by a physician or other operator; in other embodiments, automatic control is used for the scan.

For all cervical examination devices, the images can be viewed on a color monitor or other display; a touch pad, keyboard or other interactive device can enable repositioning on the display of at least a portion of at least one image, magnifying at least a portion of at least one image, marking on the image at least one location in the image, controlling device operation and any combination thereof. Control of imaging can be via the touchpad or other interactive device, via the control unit, via a control on a module and any combination thereof. In preferred embodiments, a learning algorithm is used to improve the quality and accuracy of the results. In some embodiments, the acquired data are analyzed in real time.

Controls can include, but are not limited to: selection of cervical examination device type; selection of acquisition of a single image (snapshot mode) or of multiple images (video mode); acquiring a single image; start/stop for video images; zoom control; focus control; illumination control; including filtering of light, light on/off, light intensity; and, for a timer to fix the length of an examination, timer start/stop and timer set time. Any combination of controls can be via the touchpad or other interactive device, on the control unit, on a control, on a module and any combination thereof.

One function of a timer is to start a portion of a procedure and then to inform a physician that a portion of a procedure is complete; the physician can then proceed to a next examination or a next stage in an examination.

FIG. 4 depicts an embodiment of a control unit, showing the controls on the control unit. In this embodiment, the illumination can be increased (111, LED+) or decreased (113, LED−), the view can be zoomed in or out (115, ZOOM), the system can be activated or deactivated (116, ‖ ▶ ), filtering can be applied to or removed from the light (112, FILTER) and an image can be taken (114, SNAP).

In some embodiments, at least a portion of at least one member of a group consisting of: acquired data, analyzed data, a result, a display and any combination thereof can be stored in at least one database.

Typically, the modular optical probe comprises the following cervical examination devices:

A base unit (500) configured to supply power to the control module (110) as shown in FIG. 5. In some embodiments, the base unit (500) is also configured to supply power to a processor (not shown).

A digital colposcope module (210) reversibly connectable to the control module (110). In FIG. 1, the digital colposcope module (210) is shown connected to the control module (110). It is configured to provide, when connected to the control module, a digital high-resolution imaging colposcope (200).

A transvaginal optical probe module (310) reversibly connectable to the control module (110). In FIG. 2, the transvaginal optical probe module (310) is shown connected to the control module (110). The transvaginal optical probe module (310) is configured to provide, when connected to the control module (110), a transvaginal optical probe (300) insertable into the vagina to scan the cervix. The transvaginal optical probe is at least partially coverable by a cover, preferably a sterile, single-use transparent cover. Typically, the cover will comprise a flexible polymer.

An endo-cervical endoscope module (not shown) connectable to the control unit (110). It is configured, when connected to the control module (110), to provide an endo-cervical endoscope configured to scan the cervical canal, acquire optical data, and analyze the acquired data in real time.

A control module (FIGS. 3 and 4, 110), connectable to the digital colposcope module, to the trans vaginal optical probe module, to the endo-cervical endoscope module and to the base unit. The control module (110) serves as a platform to provide control functions for whichever module it is connected to.

Software configured to process the information generated by the digital colposcope (200), the transvaginal optical probe (300), the endo-cervical endoscope and any combination thereof. The software is executable on a processor in communication with the control module (110); the results are displayable. Preferably, the processor is a dedicated processor. Preferably, the processor is in communication with at least one database to store a member of a group consisting of: at least a portion of the generated data, at least a portion of the results, and any combination thereof. Preferably, the base unit is configured to provide power for the processor. The base unit and the control unit are preferably integrated together, but can be separate. The display can be integral with the processor (for non-limiting example, a processor and a display in a laptop), or a separate display can be used (for non-limiting example, a projector).

In some embodiments, at least one of the following accessories is be used with the modular optical probe:

A single-use optical probe cover (not shown), transparent in at least one region in at least the wavelengths used to probe the tissue, for covering at least the optical probe module of the trans vaginal optical probe during use. The single-use cover is configured to provide a sterile cover for the transvaginal optical probe, while allowing free passage therethrough for the optical radiation used to probe the cervix, vagina and any combination thereof. The single-use cover is therefore transparent at least the optical wavelengths used for scanning, in at least the regions(s) through which the optical radiation will pass.

A single-use endo-cervical endoscope cover (not shown), transparent in at least one region in at least the wavelengths used to probe the tissue, for covering at least the endoscope unit during use. The single-use cover is configured to provide a sterile cover for the endoscope unit, while allowing free passage therethrough for the optical radiation used to probe the cervix, vagina and any combination thereof. The single-use cover is therefore transparent at least the optical wavelengths used for scanning, in at least the regions(s) through which the optical radiation will pass.

A support unit (FIGS. 5 and 6, 400) connectable to the control unit (110), configured to stably support the control module, the digital colposcope module (210), the optical probe module (310) and any combination thereof. FIG. 5 shows the support unit (400) supporting a digital colposcope (200). The embodiment of FIG. 5 is further configured to support a base unit (500). In some configurations, the support unit (400) is configured to support a processor; in some configurations, it is configured to support a display and, in some configurations, it is configured to support at least one module of the system when the module is not in use. FIG. 6 shows an enlarged view of a digital colposcope (200) mounted on the support unit (400). The support unit, as shown, has a tripodal base with wheels for easy repositioning of the support unit. In other embodiments, the base of the support unit can have between 1 and 10 feet. Any conventional design can be used for a base for the support unit. For non-limiting example, the base of the support unit can be a flat plate, a section that expands toward the bottom of the support unit, or any other conventional base design that provides a stable support for the support unit. Preferably, the support unit has at least one wheel, although any conventional means of enabling easy repositioning such as, but not limited to, at least one slider, can be used. In less-preferred embodiments, the support unit is lifted to be repositioned.

In some embodiments, the optical probe and the endo-cervical endoscope are similar enough in size and shape that the same cover can be a dual-use cover configured to be used as both an optical probe cover and an endoscope cover.

Other accessories can include, but are not limited to, a storage unit for modules not in use, a display unit to enable quick selection and quick storage of modules, a storage unit configured to contain a plurality of optical probe covers, a storage unit configured to contain a plurality of endoscope covers, a storage unit configured to contain a plurality of dual-use covers and any combination thereof.

The system is designed for quick and easy assembly and disassembly of each of the cervical examination devices, such as, but not limited to, the digital colposcope (200), the vaginal optical probe (300), and the endo-cervical canal endoscope. This enables rapid switching between cervical examination devices, so that an examination requiring use of two or more cervical examination devices can be completed more rapidly and more easily, increasing the physician's efficiency and decreasing discomfort for the patient.

Endo-Cervical Endoscope

In some embodiments, the endo-cervical endoscope module, when assembled with at least one other module to form an endo-cervical endoscope, can scan automatically substantially all of the surface of the endo-cervical channel. The endo-cervical endoscope module comprises a motor to move the tip of the module into the endo-cervical channel and to rotate either the entire tip including the optics contained therein or at least a portion of the optics therein, such that the optics can scan substantially all of the endo-cervical channel. Preferably, the scan follows a spiral path, with the tip progressing into the endo-cervical channel along the longitudinal axis thereof while the rotating portion rotates. Longitudinal speed and rotation speed can be constant or variable, but are preferably constant during a scan. Other paths are possible, such as a path where the endo-cervical endoscope is inserted fully into the endo-cervical channel, and a spiral path is followed, as disclosed above, as the endo-cervical endoscope is withdrawn from the endo-cervical channel. Repeated in-and-out motion is also possible, with the rotating portion rotating either at the beginning and end of each traverse, or a combined in-and-out and spiral motion.

In some embodiments, the endo-cervical endoscope is coverable, preferably by a sterile, single-use cover preferably transparent in any region through which it is desired that radiation be passable, such as a polyethylene or other polymeric cover. The cover supports the tip and gives reference in measurement of penetration depth of the tip. It also allows the cervix to be turned in right direction for smooth insertion of the endo-cervical endoscope.

FIG. 22A schematically illustrates an external view of an embodiment of an endo-cervical endoscope, while FIG. 22B schematically illustrates an internal view of an endo-cervical endoscope. As shown in FIG. 22A, the endo-cervical endoscope comprises a motor (1810), a tip (1830), and a probe portion covered by a cover (1820).

As shown in FIG. 22B, in this embodiment, the motor portion (1810) comprises a fiber (1910) to carry light from a light source (not shown). At the entrance to the probe portion, a GRIN lens (1920) or any collimating lens forms the light into a beam aligned along the longitudinal axis of the probe portion. A cable (1940) extends from the motor (1810) to a sensor (1960), which can be a CMOS sensor or a linear sensor array. The cable is configured to move at least one of the sensor (1960) and the mirror (1970) to enable scanning. The probe portion (1950) is at least partially comprised of a transparent material, such as glass or, preferably, a transparent polymer.

The endo-cervical endoscope can be inserted until the cover (support tip) is in full contact with the cervix and the endocervical probe is inserted into the endo-cervical channel, through which suspicious locations can be examined by a plurality of sensors, such as those described below. The device is provided with a sensor of mutual displacement between the cervix and the endo-cervical endoscope. Since the patient cannot be absolutely immobilized and can move relative to the probe, at least one sensor is configured to measure displacement of a tissue to be diagnosed. At least one sensor is configured to determine a location of suspicious tissue in the endo-cervical channel.

In some embodiments, a multifunctional passage in the endo-cervical endoscope can be used for tissue sampling at least one suspicious location in the cervix, for administering medicines or other materials into the cervical cavity, for administering an acetic acid wash, and any combination thereof.

The endo-cervical endoscope can comprise at least one optical fiber connected to a spectrometer for spectral analysis. Light from at least one white-light source can be reflected, refracted or scattered from the cervical tissue. Auto-fluorescence of cervical tissue can also be excited by at least one light source, typically a laser, in a UV range or in a visible range. At least one of the subsurface scattered white light and the autofluorescent light can be conducted to the spectrometer via the at least one optical fiber.

The cervical examination devices can scan and analyze tissue, such as cervical tissue, by means of multiple optical features. In one embodiment, three optical features are used.

In some embodiments, the modular optical probe, using at least one of the cervical examination devices, can scan the external os of the uterine cervix in order to identify abnormal tissue features in the cervical tissue. The minimum scannable radius 0.5 mm and the maximum scannable range is the entire external os. Software data analysis is used, leveraging effects which differ between abnormal and normal tissue. In some embodiments, a thorough colposcopic examination of the uterine cervix is conducted prior to results being displayed. In some embodiments, results are displayable in real time. Any combination of display and/or storage of results in real time or after completion of a scan can be used.

Figure 8:
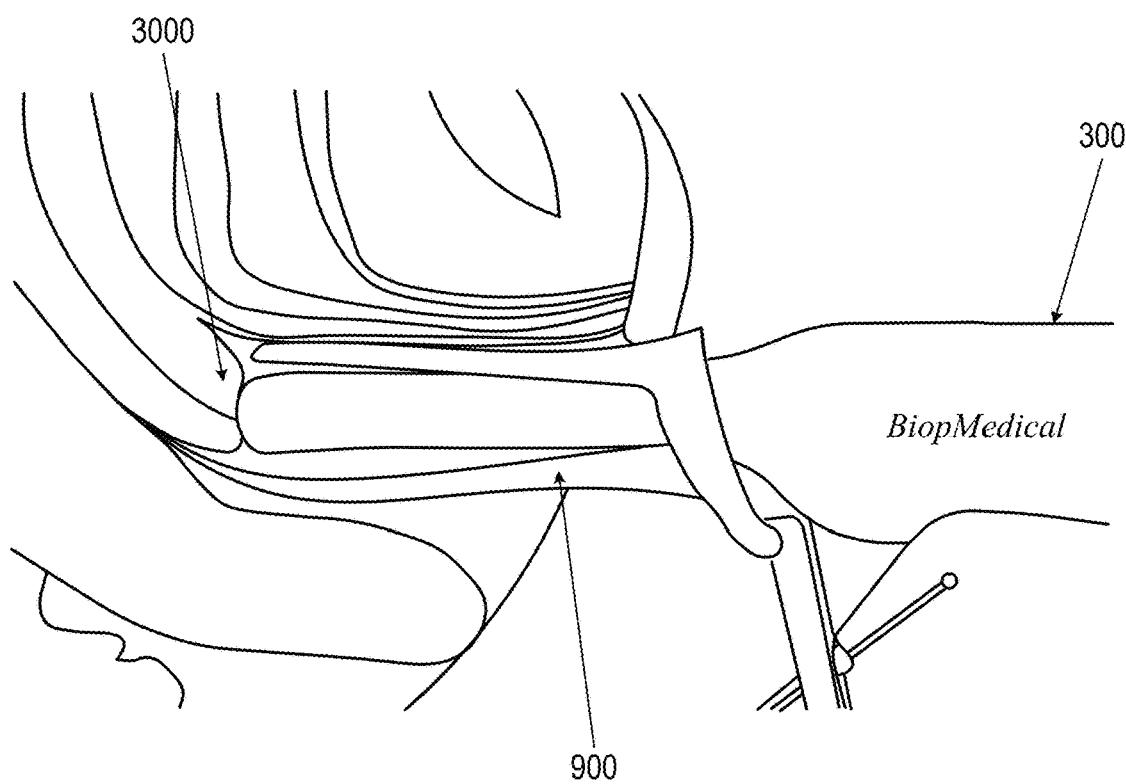
FIG. 8 schematically illustrates an optical probe in position to examine a cervix.

FIG. 8 schematically illustrates an optical probe (300) in position to examine a cervix (3000). The optical probe (300) is passed through the vagina via a speculum (900).

Figure 9A:
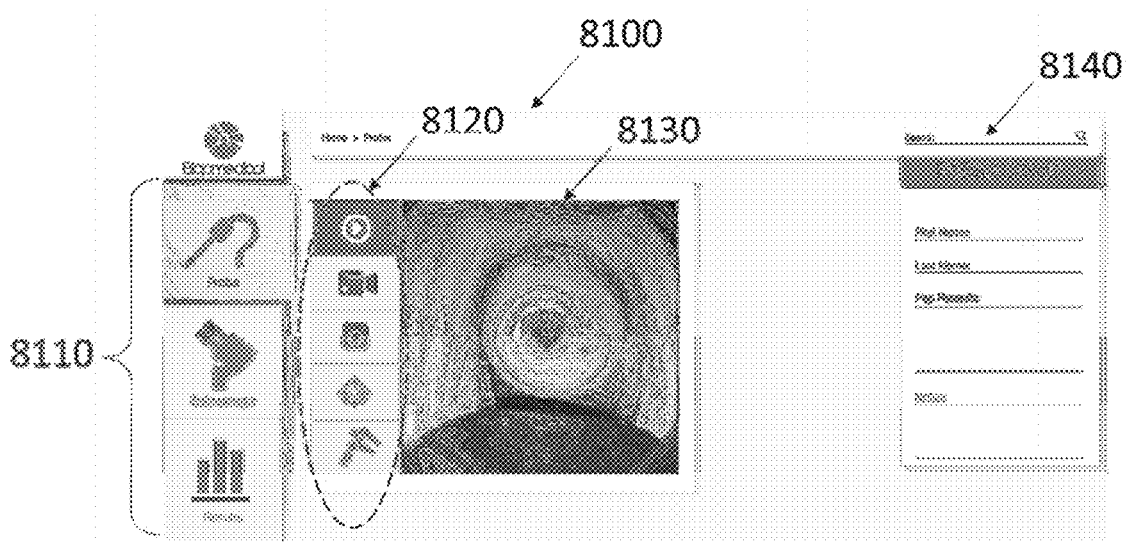
FIG. 9A-B schematically illustrates an embodiment of a graphical user interface (GUI) for accepting information and displaying results, where FIG. 9A schematically illustrates an embodiment of a screen configured to allow a user to input data about the process to be carried out, and FIG. 9B schematically illustrates an embodiment of a screen configured to show results of a procedure.
Figure 9B:
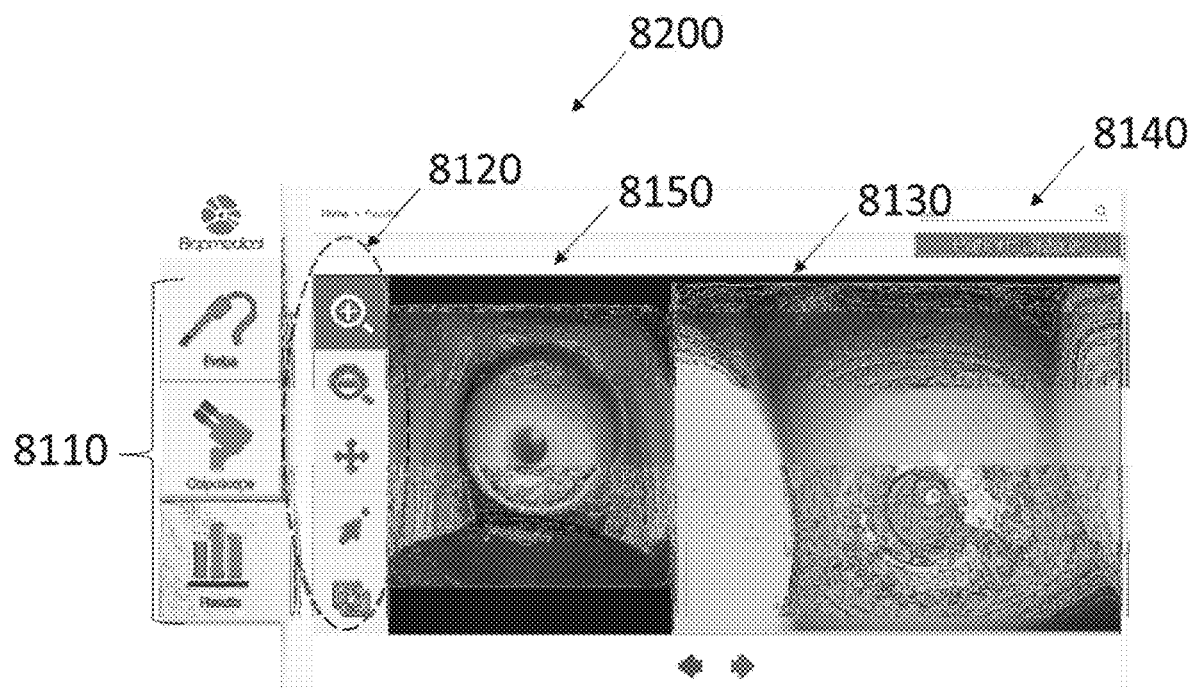

FIG. 9A-B schematically illustrates an embodiment of a graphical user interface (GUI) for accepting information and displaying results.

FIG. 9A schematically illustrates an embodiment of a screen (8100) configured to allow a user to input data about the process to be carried out. At the center (8130), an image (or live video) of the cervix is displayable. At the left (8110) are icons indicating the examination device, a colposcope or an optical probe, and an icon to display results. The icons (8120) to the immediate left of the image (8130) indicate tools, such as, from top to bottom, videoing, taking a single image, zooming, and measuring. At right (8140) is an area where a patient's details can be entered.

FIG. 9B schematically illustrates an embodiment of a screen (8100) configured to show results of a procedure. At the left (8110) are icons indicating the examination device, a colposcope or an optical probe, and an icon to display results. The icons (8120) to the immediate left of the image (8130) indicate tools, such as, from top to bottom, zoom in, zoom out, pan, mark, and compare images. At the right top (8140) is a pop-up with the patient's details. At left in the center is a color map (8150) of the cervix, showing probability of abnormal tissue as determinable via transvaginal optical probe. At right in the center is an image of the cervix after a colposcopy procedure by the digital colposcope. The two images can be registered together to show a combined result from the two images, giving a user colposcopy output images and text in a standard format, with additional detail and additional information provided by the transvaginal optical probe scan of the present invention.

Changes in cells such as cervical cells, such as the changes characteristic of a transformation to a pre-cancerous or a cancerous state, alter the morphologic and biochemical characteristics of the tissue. This process leads to changes in the optical properties of the tissue, such as, but not limited to, the spectral distribution of light scattered by tissue, the spatial and angular distribution of light scattered by tissue, the reflectivity of the tissue, and any combination thereof. The modular optical probe of the present invention relies on the modified behavior of the abnormal cells and the resulting differences in optical signature between normal and abnormal cells, with different differences presenting at different wavelengths of light. For non-limiting example:

Subsurface scattered and reflected white light spectrum: The different spectral components of white light are absorbed, reflected and scattered in distinctly different ways by healthy versus abnormal tissue. Abnormal tissue, such as precancerous and cancerous tissue, shows increased nuclear/cytoplasm ratio in the epithelial layer, increased chromatin content, destruction of collagen in the stroma and other modifications in cell structure. These changes can be identified and compared to normal, healthy tissue.

Scattering of coherent light: Morphological changes in the cells comprising a tissue modify coherent light (laser) scattering patterns and lead to changes in angular and spatial distribution of the scattered light. The changes in angular and spatial distribution, such as total scattered power and intensity decay, can help in identification of abnormal tissues.

Micro-imaging: High-resolution and/or micro-images contain optical features and tissue textures of normal and abnormal areas that will present differently due to changes in color of the tissue, in blood vessels density and shape and other changes in the tissue surface texture such as keratinization. Use of texture analysis enhances recognition of abnormal tissue.

Figure 10:
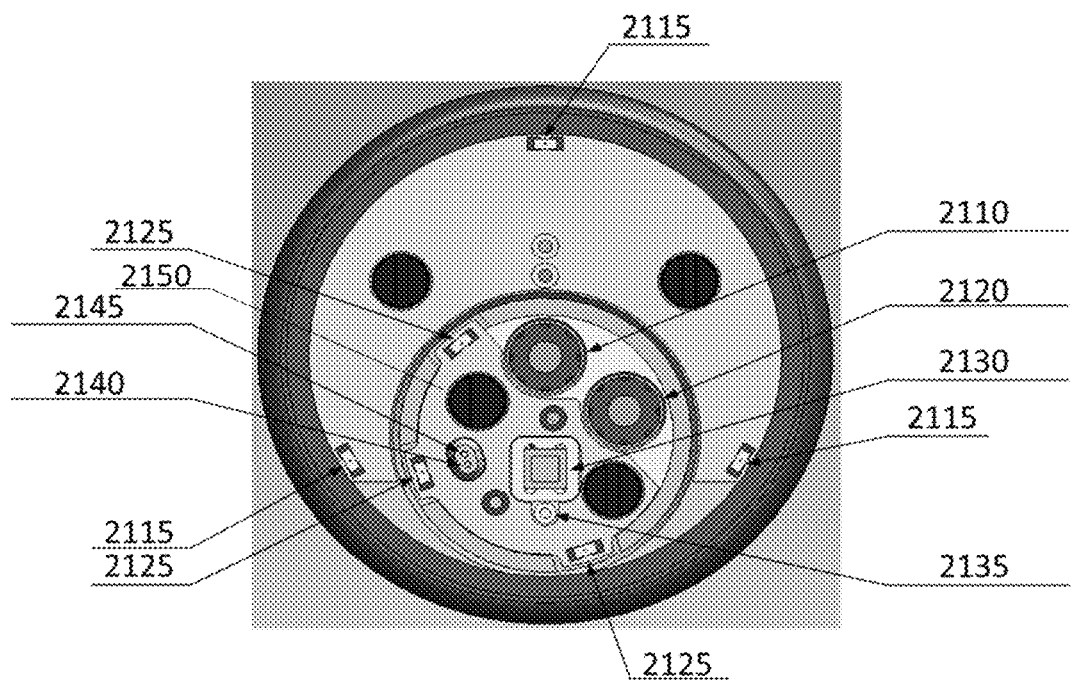
FIG. 10 schematically illustrates the optical components of an embodiment of a module of the transvaginal optical probe.

FIG. 10 schematically illustrates the optical components of an embodiment of a transvaginal optical probe module (310). In this embodiment, there are two sets of LED's, one set (2115) providing illumination for a first camera (the macro camera (2110) which acquires an overview image of substantially all of the cervix. The second set (2125) provides illumination for a second camera (the micro camera, 2120) which acquires close-up, large-scale images of selected portions of the cervix. A scattering sensor (2130) measures the spatial distribution of laser (2135) light scattered by the tissue. Light from the white light source (2145) is captured by a spectrometer (2140). In some embodiments, at least some of the laser light scattered from the tissue is transmitted to the spectrometer via an optical fiber. In some variants of such embodiments, at least one lens can be used to improve transfer of the scattered laser light into the optical fiber.

The transvaginal optical probe (300), before it is brought into contact with the cervix, can, using the macro-camera (2110), generate a macro-image of the cervix. The macro-image is used for scaling of the cervix, for presentation of the results and to register micro-images and/or HD images acquired by the micro camera (2120) with the images generated by the digital colposcope (210). Numeral 2150 refers to a multifunctional passage designed for passing materials of interest from nonboring environment to the tissue to be tested and sampling the aforesaid tissue. After contacting the cervix, the transvaginal optical probe (300) can scan the cervical tissue, using, typically, the three optical features disclosed above to identify changes specific to abnormal tissues. The captured high-resolution data is processed by software configured to analyze the captured high-resolution data and to output the results of the analysis. Preferably, the results are provided in an easy-to-interpret form such as a visual display. Results can be output, for non-limiting example, as a visual display, in tabular form and any combination thereof, Data and results can be displayed, stored and any combination thereof. The physician can perform a standard colposcopy with a digital colposcope. Once colposcopy is completed, the physician can select biopsy locations, independently of the results, in conjunction with the results and any combination thereof.

Color Map Output

Figure 11:
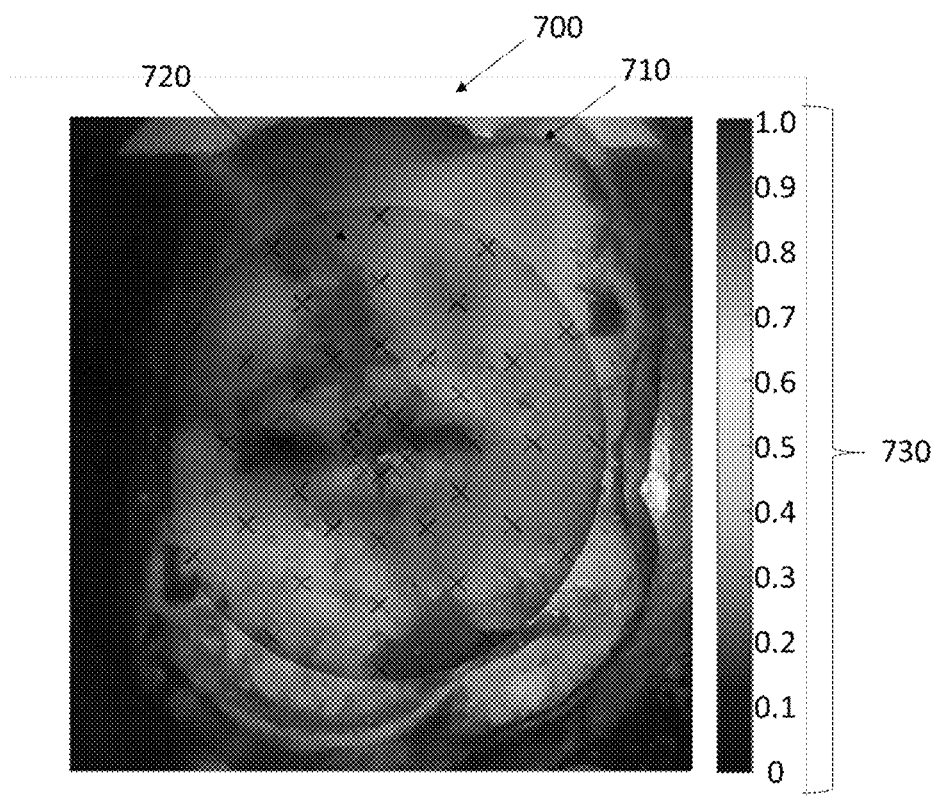
FIG. 11 depicts an embodiment of output from the system.

In preferred embodiments, the device output (FIG. 11, 700) can comprise at least one member of a group consisting of: at least one color image of at least a portion of the cervix, at least one color image of at least a portion of the vagina, a color map (720) of the cervix (710) (and/or vagina) comprising the locations of the scanning points (X's) and indicating, for the displayed portions of tissue, the probabilities of abnormal tissue and normal tissue, based on the results of the optical feature assessment.

It should be noted that an image can acquired by a single-image camera, it can be a single image selected from a series acquired by a video camera, and any combination thereof.

Preferably, a color guide (color bar indicator, 730) is presented next to the color map. The color guide indicates the color associated with each range of probabilities of abnormal tissue at a given location as a color. In the embodiment shown, blue indicates a low probability of abnormal tissue, with the colors grading through a spectrum to red, which indicates a high probability of abnormal tissue. Preferably, the colors comprise a continuous spectrum, so that the width of each probability range is inversely proportional to the number of colors available to the display. For non-limiting example, for a probability of abnormal tissue between 0 and 100%, if N colors can be displayed in a map, each range will have a width of about 100/N %. At least one location for acquisition of a biopsy can be based, at least in part, on these results.

The optical probe is insertable into the vagina and can scan the uterine cervix around the external cervical os. Typically, data are acquired for the three optical effects as disclosed above (subsurface scattered white light spectrum, scattering of coherent light and microscopic images) and are analyzed as disclosed above to determine the optical properties of the tissue and therefore determine probability of normal and abnormal tissue in the examined tissue. The results, showing probability of normal and abnormal tissue as measured by each of the optical properties, are combined using software with interpretation capabilities. The output of this process is a color map superimposed on an image, as disclosed above.

The digital colposcopy map, the transvaginal optical probe map, the endo-cervical endoscope map and any combination thereof can be used by a physician can as an aid in determining biopsy locations. It should be noted that, in addition to individual maps, an overall picture or unified result can be generated by means of a registered combined map. A registered combined maps can comprise a digital colposcopy map, a transvaginal optical probe map, an endo-cervical endoscope map and any combination thereof.

Scaling

In preferred embodiments of the present invention, the system can automatically detect the dimensions of a scanned cervix with a laser and camera. The principle of distance determination is well known in the art for a camera and a laser located at a known distance from each other and in a known orientation to each other. The laser beam impinges onto at least a portion of an object and an image is captured of the object and laser spot.

Figure 12:
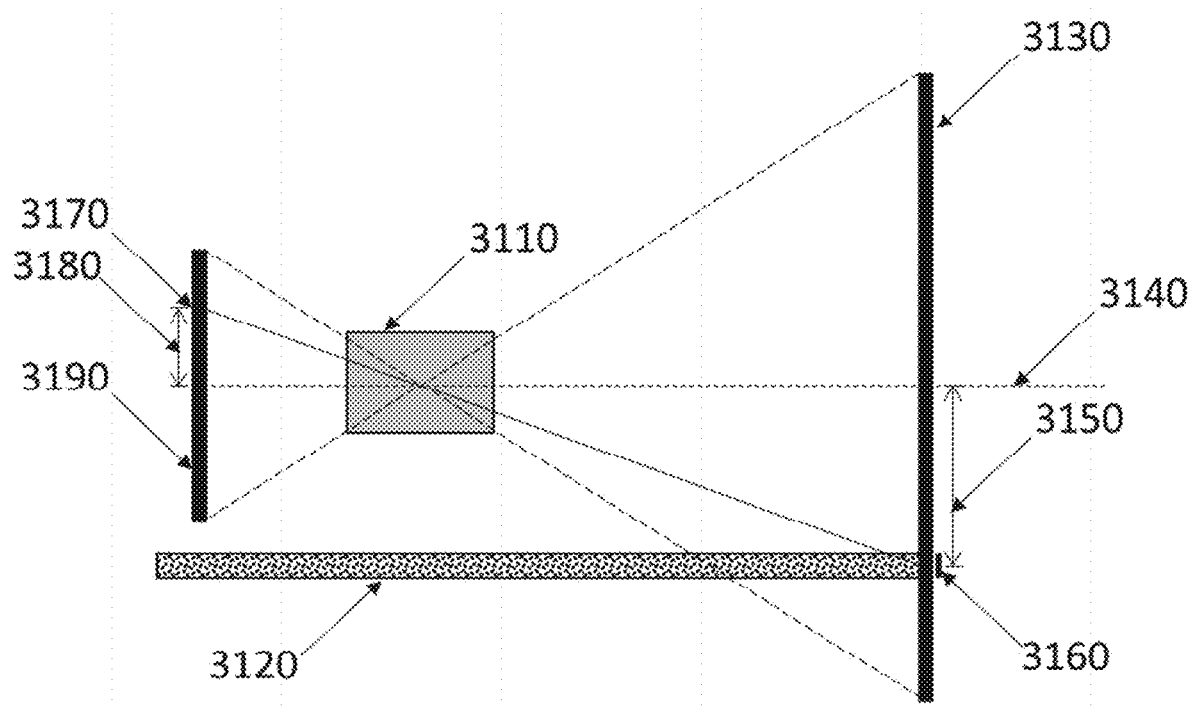
FIG. 12 shows an embodiment of a method for finding a scale factor for converting between image size and object size.

FIG. 12 shows, in side view, an embodiment of a method for finding a scale factor for converting between image size and object size. FIG. 12 shows a sensing device (3110) which can acquire an image (3190) of an object in a field of view (FOY) (3130) of the sensing device (3110). A laser beam (3120), perpendicular to the FOV (3130) is shone on the object, with the object perpendicular to the sensing device (3110), making a spot (3160) on the object. The spot (3160) is a distance X (3150) from the center line (3140) of the sensing device (3110) (and, preferably, the centerline of the image). The center of the image of the spot (3170) is at a distance Y (3180) from the center line (3140). If the distance Y (3180) is measured in pixels and the distance X (3150) is measured in a distance unit such as, but not limited to, mm, then a scale factor S converting image pixels to distance units can be calculated from S=X/Y so that a physical dimension u of an object can be calculated from u=S v, where v is the dimension, in pixels, of the image of the object.

In another embodiment, from the known size of the laser spot, the physical size of the portion of the object covered by the laser spot can be determined from the number of pixels in the image between the center of the laser spot and the edge of the laser spot. If the object is fairly flat, the physical size of the part of the object in the image can be determined from the fraction of the image covered by the laser spot.

Therefore, the actual physical size of the cervix is determinable from at least one image comprising at least a portion of the cervix and at least one laser spot of known dimensions. A plurality of images comprising different portions of the cervix can be used to improve the accuracy of the size determination. Furthermore, if size determinations are made substantially simultaneously with at least two images of at least one portion of the cervix or vagina, movement of the patient between acquisition of the first image and acquisition of the second image can be determined and the images can be corrected for movement, further increasing the accuracy of the results. Corrections can be made for inhomogeneity of the laser light, e.g., from reflections from other light sources, increased reflection from wet tissue, non-flatness of tissue, etc.

Other corrections can include: correction for tissue type and correction for thickness of the glass or other transparent material covering the head of the probe.

Optical Design of the System with Glass

In preferred embodiments, the cover is glass; other transparent materials such as transparent polymers can be used. The term "glass", as used herein, will refer to any transparent cover material.

The condition of the tissue can affect the scattering properties of coherent light. The spatial and angular distributions of the scattered light are affected by different elements of the tissue. The main elements affecting scattering are:
1. Scattering by cells in the epithelium.
2. Scattering by the cell nucleus.
3. Scattering by chromatin content in the nucleus and in the extra-nuclear tissue in cells.
4. Scattering by collagen in the stroma.

In particular, the scattering is affected by the size of the cell nucleus, where scattering angle decreases with increasing nucleus size. The nucleus in normal cells has a diameter of about 1-3 µm, while, in CIN cells, the nucleus has a diameter of about 3-10 µm.

Another significant determinant of scattering is the amount of fibrous stroma collagen (the tissue depth), where scattering angle increases with the amount of fibrous stroma collagen. Normal cells have significantly more collagen in the stroma than abnormal tissues.

A preferred sensor for measuring scattering comprises a two-dimensional pixel matrix (CMOS or CCD). It is preferably located in a Fresnel zone relative to the cells in the tissue and is preferably in a near zone relative to the illumination beam diameter.

A laser sensor, a sensor sensitive to the laser wavelength, can be used to determine the scattering of coherent light from the tissue, typically the subsurface tissue. An optimal location for the scattering sensor can increase sensitivity to differences in cell nucleus size.

The approximate scattering angle will be larger for the smaller normal nucleus than for the larger abnormal nucleus, and the difference in angle increases as the wavelength of the light decreases. Therefore, typically, scattering from the nucleus will be measured in the near infrared (NIR), although other wavelengths can be used. For example, at a wavelength of about 980 nm), the approximate scattering angle will be more than about 15° for the smaller normal nucleus and less than about 15° for the larger abnormal nucleus.

In preferred embodiments of the system of the present invention, the laser sensor is placed in Fresnel zone with respect to the cells diameter in the tissue and in near zone relative to illumination beam diameter. The scattering sensor is located at distance D in the lateral direction in order to collect light which is scattered from the tissue by angles larger than about 15°.

Figure 13:
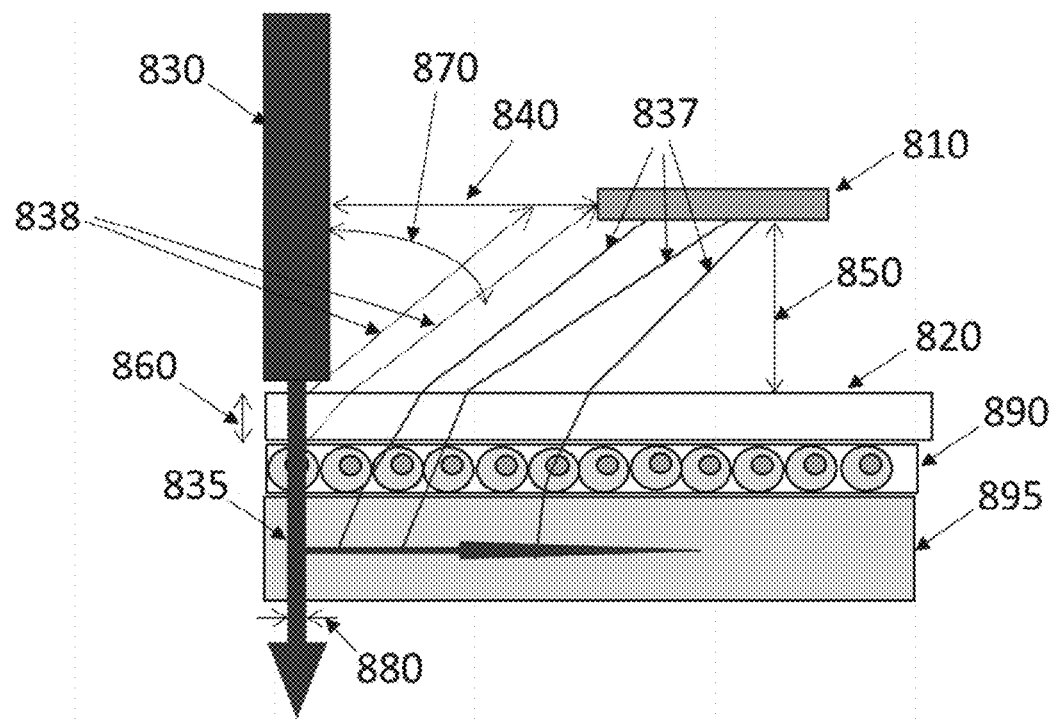
FIG. 13 schematically illustrates the distances and angles for calculation of the laser-sensor lateral distance D.

FIG. 13 schematically illustrates the distances and angles for calculation of the laser-sensor lateral distance D. The laser (830) emits a laser beam (835) which passes through the glass cover (820) of the device and is scattered by epithelial tissue (890) and by the stroma (895). The light reflected from the glass (838) and by large nuclei does not reach the sensor (810), while light scattered from the tissue (837) reaches the sensor (810).

The laser-scattering sensor lateral distance D can be calculated from:

$$D = 0.5 \cdot Bd + ta \cdot \tan(Aa) + tg \cdot \tan\left[a\sin\left(\frac{\sin(Aa)}{n}\right)\right] \quad (1)$$

where:
Bd—diameter of illumination beam (880),
ta—distance from glass to sensor (850),
tg—glass thickness (860),
Aa—angle of light scattered back after reflection by nucleus (870).

In general, the sensor total power can give an indication of the fraction of abnormal cells in the area covered by the laser spot. For a laser-sensor lateral distance D, as calculated above, the difference between the amount of light collected by the sensor for normal cells and the amount of light collected by the sensor for abnormal cells is maximized, thus maximizing the sensitivity of the laser scattering portion of the system to abnormal cells.

Short-wavelength light (for example, in the blue to violet range, 390 nm-490 nm) has smaller diffraction angles, for nuclei and for cells. So, even for normal cells, the light backscattered by nuclei and cells will not reach the sensor and the intensity distribution differences will be caused by changes in the dimensions and in the number of smaller particles in the tissue.

Figure 14:
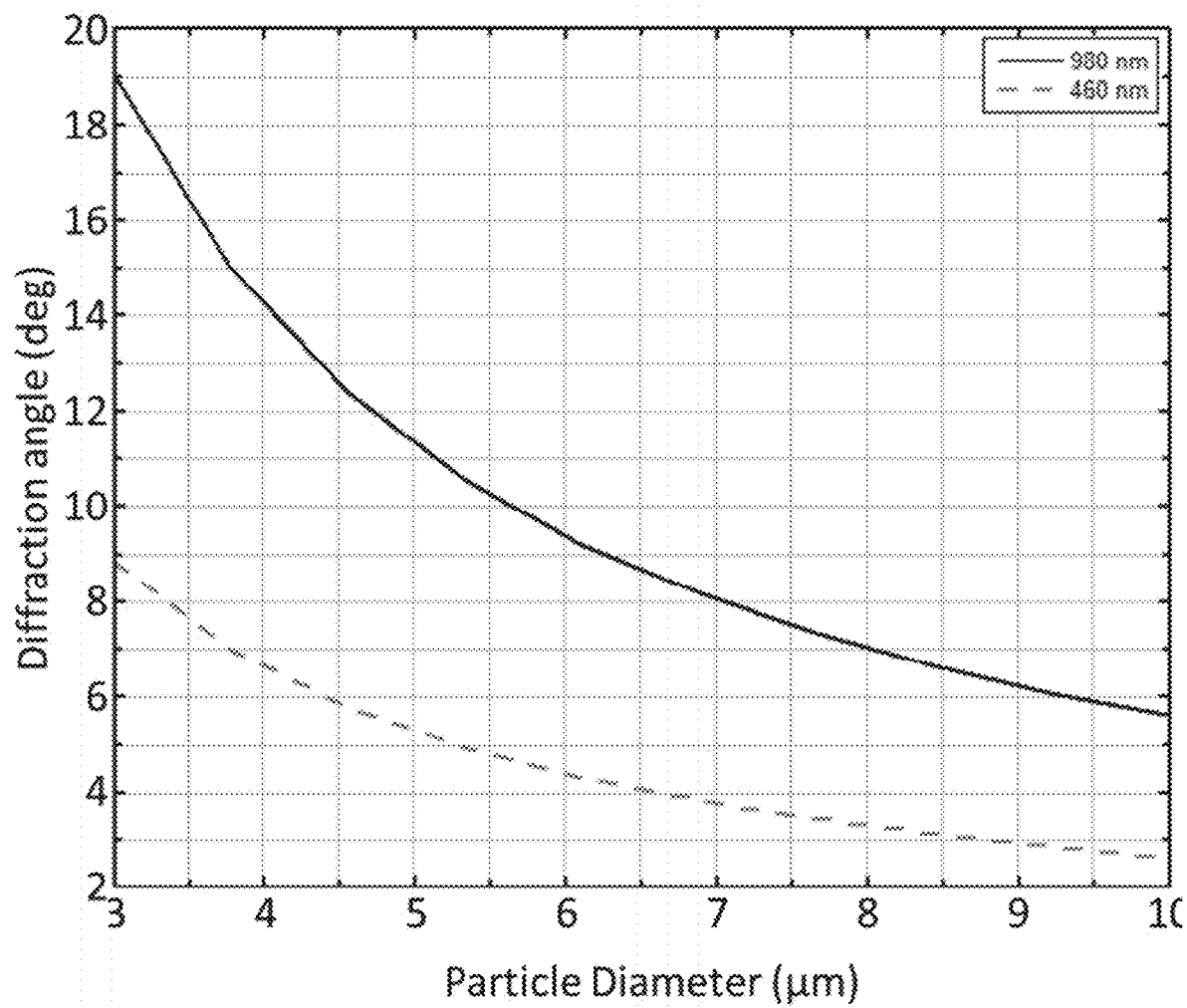
FIG. 14 illustrates diffraction angle versus particle diameter.

FIG. 14 illustrates the effect of particle diameter on diffraction angle for 980 nm light (solid line) and 460 nm light (dashed line).

The main small features in the epithelium and stroma are chromatin and collagen.

Figure 15:
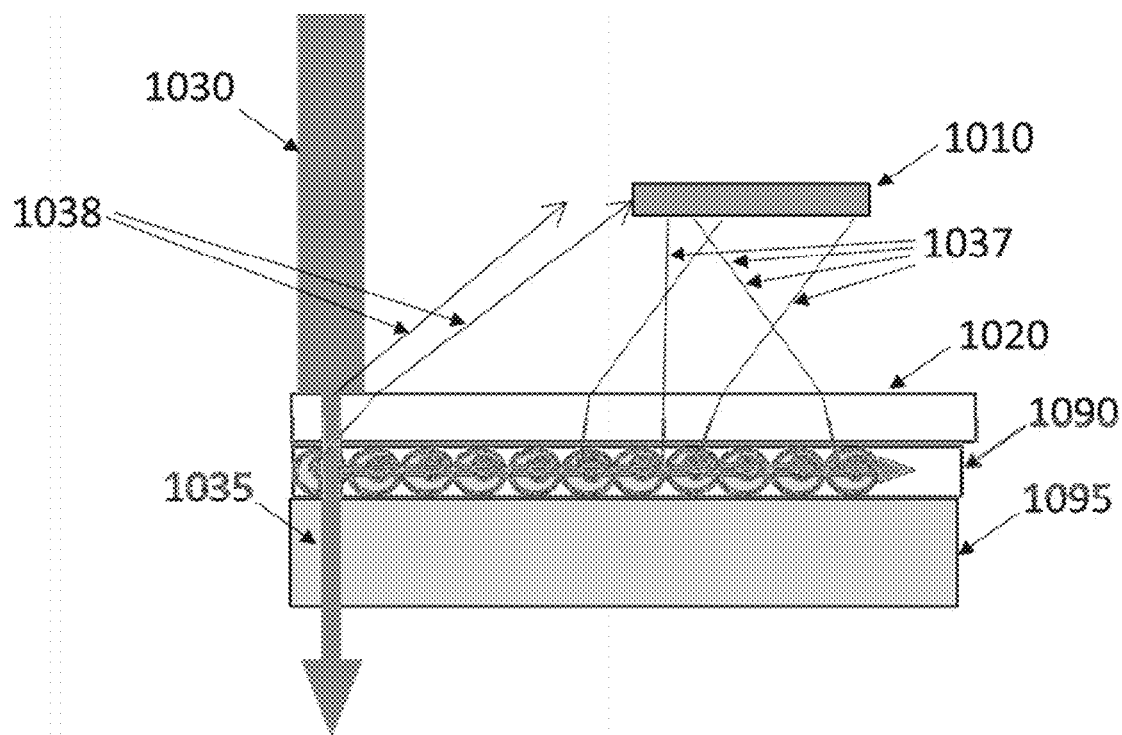
FIG. 15 schematically illustrates scattering of light from small particles in the tissue.

FIG. 15 schematically illustrates scattering of light from small particles in the epithelial cells.

The laser (such as a blue laser) (1030) emits a laser beam (1035) which scatters off the glass cover (1020) of the device and off the epithelial tissue (1090); scattering from the stroma (1095) contributes little to differences in signal between normal and abnormal cells when the blue light is used for the illumination. However, for an NIR laser, differences in the signal between normal and abnormal cells will be more dependent on scattering from the stroma Light scattered from the glass (1038) does not reach the sensor (1010), while light scattered from the tissue (1037) reaches the sensor (1010).

Scattering by small particles like chromatin content or collagen fibers can be estimated in the Rayleigh approximation due to the small dimensions of these particles relative to the wavelength of the light.

Figure 16:
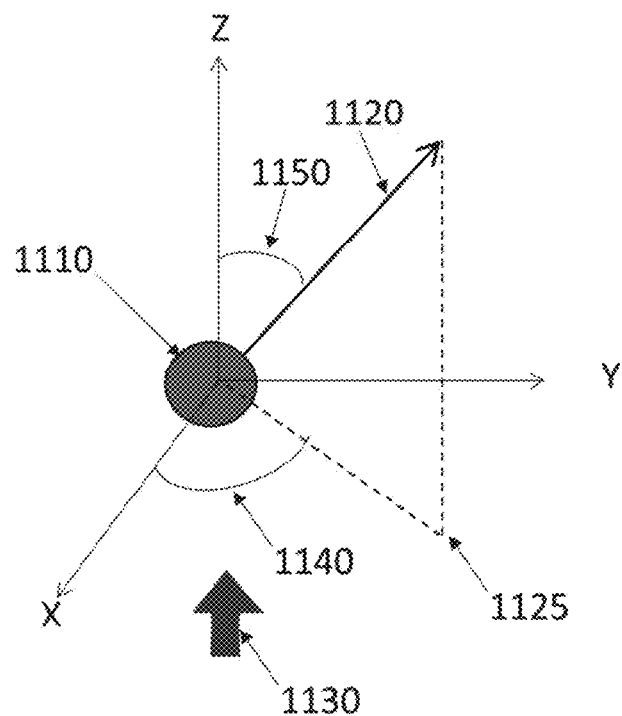
FIG. 16 schematically illustrates Rayleigh scattering.

FIG. 16 schematically illustrates Rayleigh scattering. An incident beam (1130) with intensity $I_0$ impinges on a particle (1110). The light is scattered (1120). The angle of the light with respect to a Z axis is θ (1150), The projection (1125) of the scattered beam onto the XY plane makes an angle φ (1140) with the X axis.

The intensity of the scattered radiation in Rayleigh approximation is:

$$Is = Io \cdot \frac{8\pi^4}{\lambda^4} \cdot a^2 \cdot \frac{1 + \cos^2(\theta)}{r^2} \text{ where } a = \frac{3}{4\pi} \cdot V \cdot \frac{m^2 - 1}{m^2 + 2}, \quad (2)$$

r—distance between the particle and the sensor,
λ—wavelength of the light,
θ—angle with the Z axis (1150),
φ—angle with the X axis (1140),
V—particle volume,
m—ratio of refractive index of particle to refractive index of surrounding media.

In this approximation, the angular distribution shape is similar for normal and abnormal cells. The difference between normal and abnormal cells can be seen in a difference in intensity due to the difference in collagen volume, since the abnormal cells have less collagen than the normal cells. The intensity will also depend on the wavelength and on the incident intensity, although these will not significantly affect the difference between normal and abnormal cells.

Figure 17:
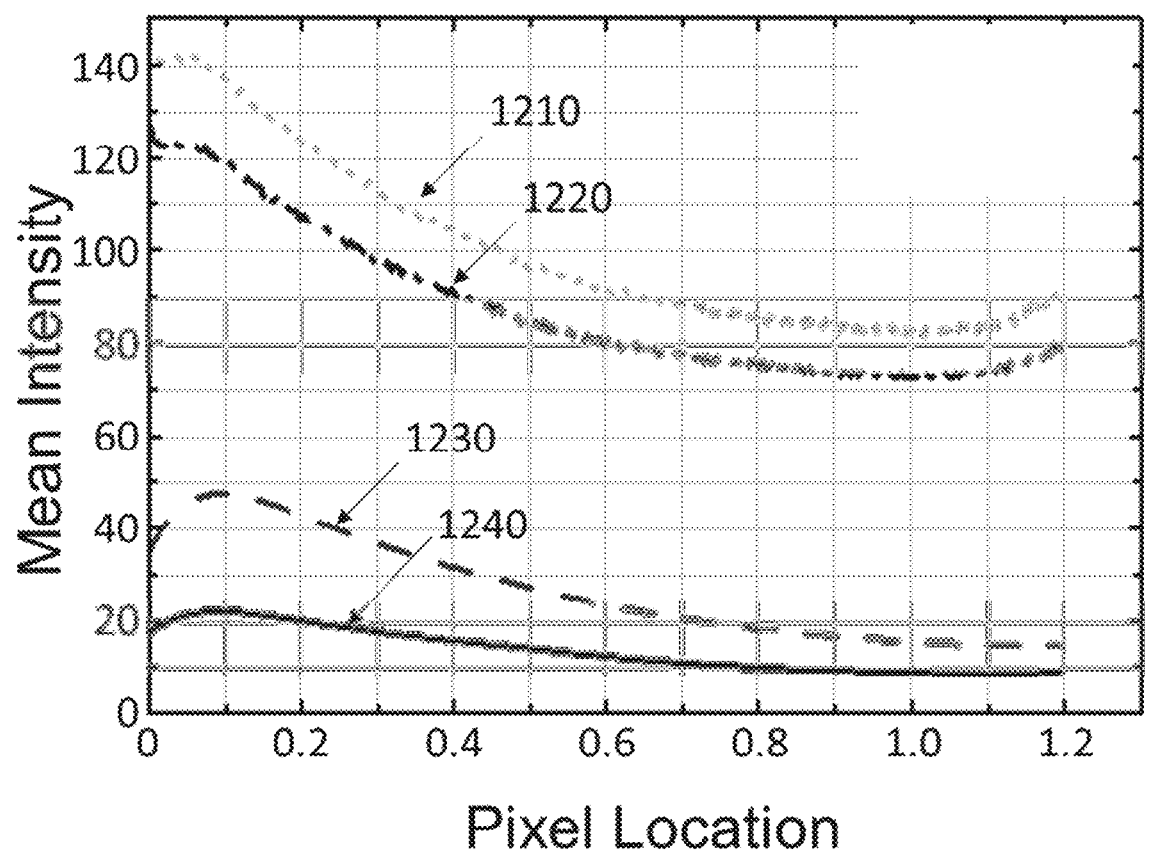
FIG. 17 depicts mean intensity distribution as measured for cells from the normal scanned points and the abnormal scanned points.

The absorption coefficient of blue light is significantly higher than for NIR light and it also increases significantly when the cells are abnormal. Therefore, the penetration depth for blue light is significantly smaller than for NIR light and the blue image is more strongly affected by the epithelial layer than by the stromal layer (FIG. 14). Abnormal cells in the epithelial layer will have more chromatin volume that will scatter the blue light back to the sensor and will cause increase of the blue light power reaching the sensor. This is demonstrated by experiments on four women with a total of 200 scanned points (40 abnormal and 160 normal). FIG. 17 shows mean intensity distribution vs. Pixel location [mm] as measured for cells from the normal scanned points (1220, 1240) and the abnormal scanned points (1210, 1230).

The absorption coefficient of NIR light (1210, 1220) does not significantly change when the epithelial tissue is abnormal; the normal (1210) and abnormal (1220) scattered NIR light intensity varies similarly across the sensor. So, NIR light distribution will be affected mostly by the stroma. Less collagen volume in stroma leads to decrease of the light power scattered back to the sensor and will lead to additional darkening of the image in case of abnormal tissue. Although the chromatin scattering of NIR in epithelium increases for abnormal cells, the total power will be mostly defined by stroma and by nuclear light filtering.

However, the absorption coefficient of blue light (1230, 1240) does significantly change when the epithelial tissue is abnormal; the normal (1240) and abnormal (1230) scattered blue light intensity varies differently across the sensor, especially for locations less than 0.4 (40% of the distance from the center of the sensor to the edge).

Figure 18:
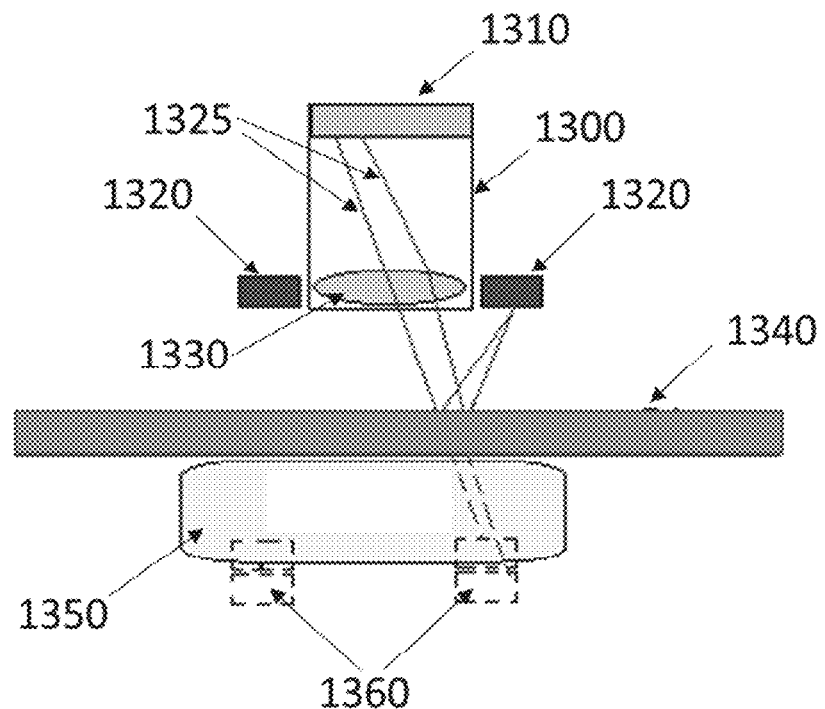
FIG. 18 schematically illustrates a prior-art configuration of an imaging camera with a sensor and lens with LED's surrounding the camera.
Figure 19:
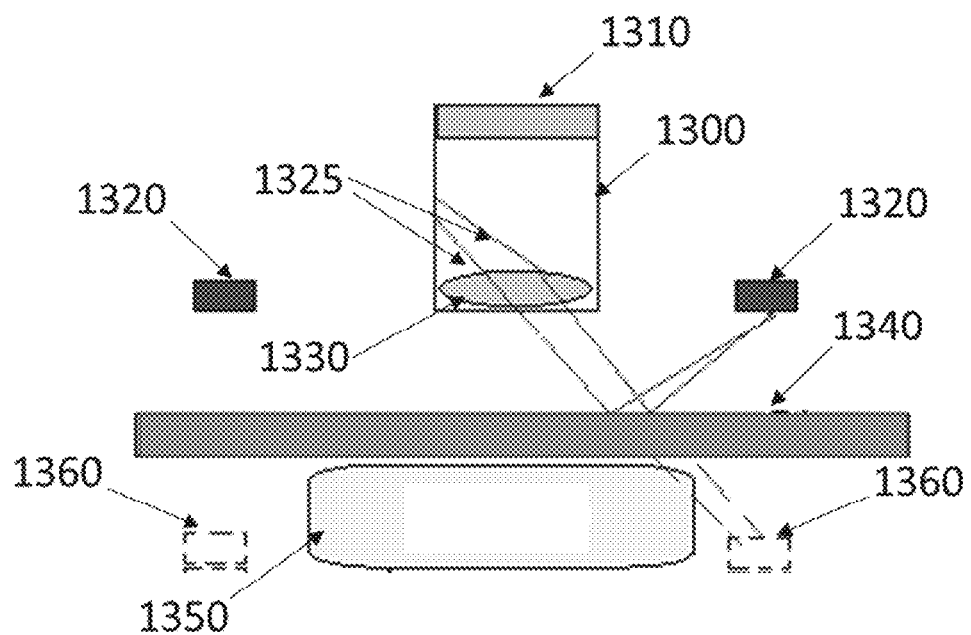
FIG. 19 schematically illustrates, for the device of the present invention, a configuration of an imaging camera with a sensor and lens with LED's surrounding the camera.

FIG. 18 illustrates how, in the prior art, unwanted light can reach a detector, while FIG. 19 illustrates how, in the present invention, unwanted light is prevented from reaching a sensor FIG. 18 schematically illustrates a prior-art configuration of a sensing device (1300) such as, but not limited to, an imaging camera, a spectrometer, or an intensity sensor. The sensing device (1300) comprises at least one sensor (1310) and at least one lens (1330). LED's or other light sources (1320) surround the sensing device (1300). The sensing device (1300) is separated from the tissue (1350) by a glass cover (1340). Light (1325) reflected from the glass enters the sensor (1310), thereby affecting the sensor response. For an imaging sensor such as is found in a camera, the light sources (1320) would appear in the image at the positions of the dashed boxes (1360).

In the system of the present invention, as schematically illustrated in FIG. 19, the sensing device (1300) with at least one sensor (1310) and at least one lens (1330) has light sources (1320) such as LED's surrounding the sensing device (1300). The sensing device (1300) is separated from the tissue (1350) by a glass cover (1340). However, the light sources (1320) are separated from the sensing device (1300) by a distance large enough that the light (1325) reflected from the glass does not reach any of the sensors (13B)); if at least one sensor (1310) were to receive light (1360) from a light source (1320), the light source would appear to be outside the tissue (1350) of interest.

Tiling of the data using micro-images from the probe and registration on the digital colposcope image.

In some embodiments of the system, the system can do a scan after recording a macro-image of the full cervix. The macro-camera is designed to have long depth of focus and it is located at larger distance from the cover glass than the micro-camera. The micro-camera has high magnification and it is focused close to outer surface of the cover glass in order to have best focus on the tissue contacting the glass. Some cervix areas can be at a small distance from the glass due to the curvature of the cervix. These areas will be out of focus for the micro-camera, but they will be in focus for the macro-camera. During the scan, both cameras will record images of the same areas in the cervix. All images will be processed and the macro-images will ensure that all areas of the cervix can be shown in focus. Therefore, the system can do a scan of at least one area at a much higher magnification. The high-magnification images and the lower-magnification images can be registered and stitched together to provide a panoramic view of the region with high magnification. In out of focus areas, where it may be needed, the lower magnification images can be used. In some variants of the system, at least one additional high-magnification image of at least one area of interest, such as an area which may contain abnormal tissue, can be made and can be registered and stitched to the panoramic image.

Each micro-image has coordinates determined by the scan profile. By identifying the location of the micro-image in the panoramic picture, the deviation coordinates of the profile scan caused by patient movement or a physician's hand movement, can be found and, if necessary, modified or repaired.

An embodiment of a process for producing at least one micro-image and stitching the at least one micro-image into the original scan comprises steps of:

Illuminate a region such as the cervix by white light, such as light from a white light LED, light from a plurality of LEDs at different wavelengths (e.g., red, green, blue), a tungsten filament bulb, or any other white light source known in the art.

Select a Field Of View (FOV) for the micro-image that is larger than the desired micro-image area to ensure that the desired area is covered, even if the patient moves during the scanning procedure.

Acquire at least one high-resolution image of the area (FIG. 20A).

Use contrast enhancement and illumination correction to improve the at least one image (FIG. 20B);

Execute distortion correction.

Each individual image can be used for local diagnosis based on analysis of the texture of the tissue and on abnormality in the shape of any structures.

Stitch the micro-image(s) in order to create a full image of the entire cervical scan with high resolution (FIG. 21). Then the stitched images are imposed on the low resolution panoramic macro-camera image for the mapping purpose. In some embodiments, the macro-image(s) are also stitched together in order to made the registration process easier because the macro-images have larger Field of View (FOV) than the micro-images and more similar resolution to the panoramic image.

The stitching process is based on the known relative positions in the grid of the micro-images and macro images; the coordinates of the scanned areas are known relative to the center of the scanner and to the rotation angles of the images. Neighboring images on the grid are stitched using registration and blending. Registration can be done using different methods: local descriptors like Scale Invariant Feature Transform (SIFT) and Speeded-Up Robust Features (SURF), pre-defined landmarks like the OS or by using intensity based registration. Image registration geometrically aligns the neighboring images and the final result is reconstructed using the overlapping regions. Different methods can be applied to obtain the stitched images. The differences between the original location of the image on the grid and the transformed image (following the stitching process) can define the actual instrument movement between these two images (if it has occurred) during the scans. If the movement is larger than the FOV of the micro camera, the micro-image cannot be used for diagnosis of that specific point. In this case, the stitched macro-images are imposed first on the panoramic image. Because we know the coordinates of the micro-images and macro-images we can now combine the stitched micro images with the panoramic image.

The final image is displayable for visual examination and can also be used for diagnostic purposes and for mapping of the normal and abnormal areas of the cervix.

In preferred embodiments, a color map of the probability of abnormality in an area is superimposable on a final image of the region of interest, such as the cervix or a vagina. An embodiment of a method of producing a final image overlaid by a color map comprises:

Producing a final image, as disclosed above, for the colposcopic image acquired before application of acetic acid (the pre-wash image).

Producing a final image, as disclosed above, for the colposcopic image acquired after application of acetic acid (the post-wash image).

Finding a registration between the pre-wash image and the post-wash image.

Determining the probability of abnormality in at least one of the colposcopic images, as disclosed above. The probability of abnormality can be determined from the transvaginal optical probe scan, as described below, from any difference between a pre-wash image and a post wash image, and any combination thereof.

Entering process data from the transvaginal optical probe scan.

Creating a probability map of the probability of abnormal tissue.

Registering the final image and the probability map.

Creating a display of the probability map overlaid on the final image.

The probability map can be any conventional level-indicating map, for non-limiting example: a color map with blue signifying a low probability of abnormality and red a high probability of abnormality, a color map over a different range of colors, a contour map with labelled rings, and any combination thereof.

Figure 22:
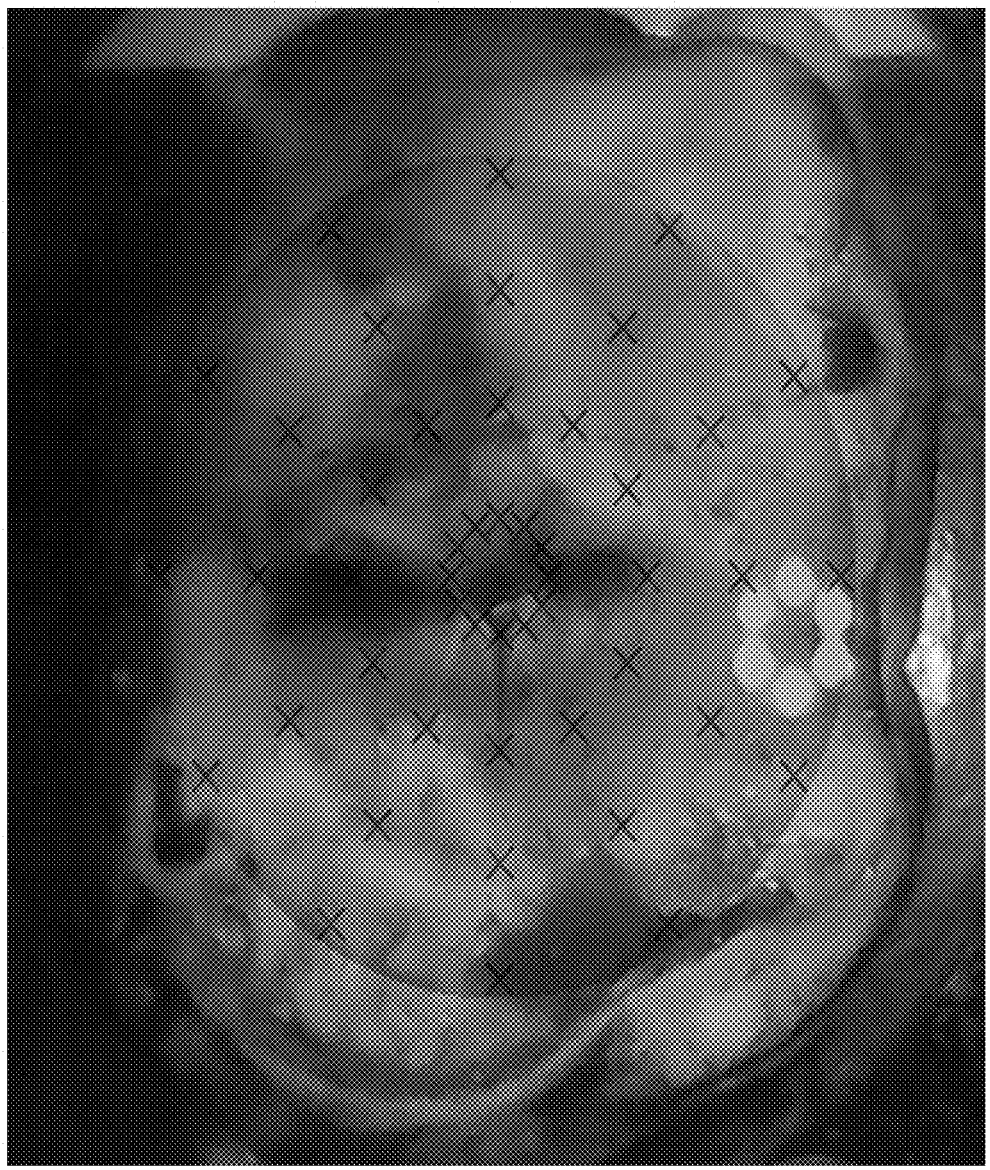
FIG. 22 depicts a probability map overlaid on a map of the cervix.
Figure 22:
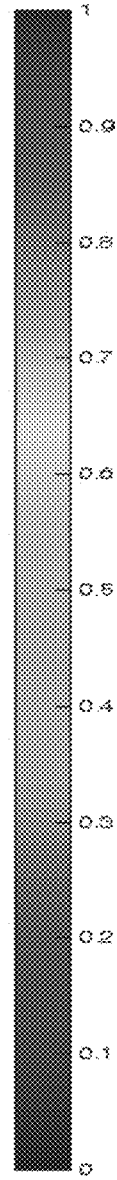

FIG. 22 shows a probability map overlaid on a map of the cervix. In the exemplary embodiment of FIG. 22, the probability of abnormality is numerically coded on a scale of 1-100, and is color coded, as indicated by the color bar, by a spectrum from blue to red, with blue indicating normal tissue and red indicating abnormal tissue.

Tracking Algorithm Flow

The workflow of the tracking algorithm can comprise the following four steps:

1. Capturing a panoramic image of the cervix by a panoramic camera.
2. Marking a target point for examination.
3. Assisting navigation of the device to the target point with dynamic marking of the target point in video flow captured by the panoramic camera;
4. Determining live scan coordinates according to obtained data of mutual displacement of the device after full contact.

The workflow of processing is the following:

1. Target detection: A region of interest (ROI) is marked around the target point in the panoramic image and Speeded Up Robust Features (SURF) are detected within it. This ROI is next searched for in the video stream by matching the SURF points of the ROI to SURF points detected in the video frames. When correspondence between a predetermined number of SURF feature located in the ROI and in at least one frame of the obtained live video flow is within a predetermined tolerance, the ROI is detected on the video frame and the tracking process begins. Other feature extraction algorithms are also within the scope of the present invention.
2. The marked ROI is tracked in live video flow by the Kanade-Lucas-Tomasi (KLT) procedure (see C. Tomasi et al, Detection and Tracking of Point Features, *Carnegie Mellon University Technical Report CMU-CS-91-132*, April 1991). The algorithm tracks corner points (J.

Shi et al, Good Features to Track, *Proceedings of the IEEE Conference on Computer Vision and Pattern Recognition*. June 1994, pp. 593-600) around the selected target point. In order to handle larger displacements, a pyramid representation of the two frames is used. The tracking algorithm provides geometric transformation from frame to frame computed from matching corner points between frames. The new location of the target point is computed using this transformation and is displayed on screen to aid navigation. If the target point is lost due to large movements of the patient, the algorithm goes back to the target detection stage (1). When the target is redetected, the system returns to the tracking stage. This process is repeated until full contact with the cervical wall is reached. After full contact, measurement of lateral displacement of tissue to be examined relative to the device is performed. The obtained mutual displacement data are used for updating the position of the scanning coordinates.

According to some embodiments of the present invention, at least one sensing device is selected from a group consisting of a panoramic camera, a camera for capturing scattering patterns, a close-up camera, a video camera, an optical fiber connected to a spectrometer, a light source, preferably a laser, effective for auto-fluorescence excitation and any combination thereof. Wavelengths effective for exciting autofluorescence range include the UV and visible light.

According to some embodiments of the present invention, the device comprises a sensor of mutual displacement of said tissue area to be diagnosed and the device.

According to some embodiments of the present invention, the method comprises a step of measuring displacement of the tissue area to be diagnosed relative to the device.

According to some embodiments of the present invention, the step of detecting a marked target area comprises a speeded up robust features procedure.

According to some embodiments of the present invention, the step of tracking and marking the target area comprises a Kanade-Lucas-Tomasi tracker procedure.

EXAMPLES

Example 1—Specification for an Embodiment of the System of the Present Invention Dimensions

| Control unit | |
| --- | --- |
| Height (mm) | 89.3 |
| Width (mm) | 60.6 |
| Length (mm) | 298.8 |
| Colposcope Unit | |
| Radius (mm) | 85.9 |
| Length - without applicator (mm) | 185.3 |
| Colposcope (Control unit + Colposcope unit) | |
| Height (mm) | 89.4 |
| Width (mm) | 60.8 |
| Length (mm) | 336.4 |
| Probe Unit | |
| Height (mm) | 66.9 |
| Width (mm) | 60.7 |
| Length (mm) | 385.6 |
| Optic probe (Control unit + Optic probe unit) | |
| Height (mm) | 89.4 |
| Width (mm) | 60.9 |
| Length (mm) | 536.7 |

In one embodiment, the processor comprises the following software:
Windows 10
MATLAB Compiler Runtime R2014b 64 bit
Arduino 1.6.11 64 bit
Basler Pylon 5 (Colposcope camera)
Visual C++ Redistributable Packages for Visual Studio 2013 or
Visual C++ Redistributable Packages for Visual Studio 2015

In preferred embodiments, the system can input standard line voltage, for non-limiting example, 110-240 VAC, 50/60 Hz.

In preferred embodiments, the Maximum probe exposure time is 90 s.

In preferred embodiments, the system can operate under the following environmental conditions:

| | |
| --- | --- |
| Temperature: | 50° F. (+10° C.) to 95° F. (+35° C.) |
| Humidity: | 95% max |
| Atmospheric Pressure: | 70 kPa to 110 kPa |
| Maximum probe exposure time | 90 seconds |

Example 2—Optical Probe Laser

Wavelength—980 nm
Beam divergence (α)—4.4 mrad)(0.25°)
Optical Power—1 mW
Continuous Wave
Exposure time>10 s
The Optical probe laser is classified as a Class I laser because it meets the qualifications for a class I laser, where a class I laser is defined as:
MPE retina (>10 sec): 4.1 mW
MPE skin (>10 sec): 7236 W/m$^2$
and the Optical Probe laser is:
MPE retina: 1 mW
MPE skin: 5100 W/m$^2$ Example 3—White Light Source In some embodiments the white light source is a fiber-coupled white light source including 4 dies.

Example 4—Digital Colposcope

Illumination for the digital colposcope can be provided by a LED light source found on the body of the device which includes three white LEDs, each including 2 dies.

Example 5—Optical Probe

Illumination for the optical probe can be provided by a total of six white LEDs—3 for the micro-camera and 3 for the macro-camera.

Example 6—Block Diagram of Electronics for Modifies

Base Unit

Figure 23:
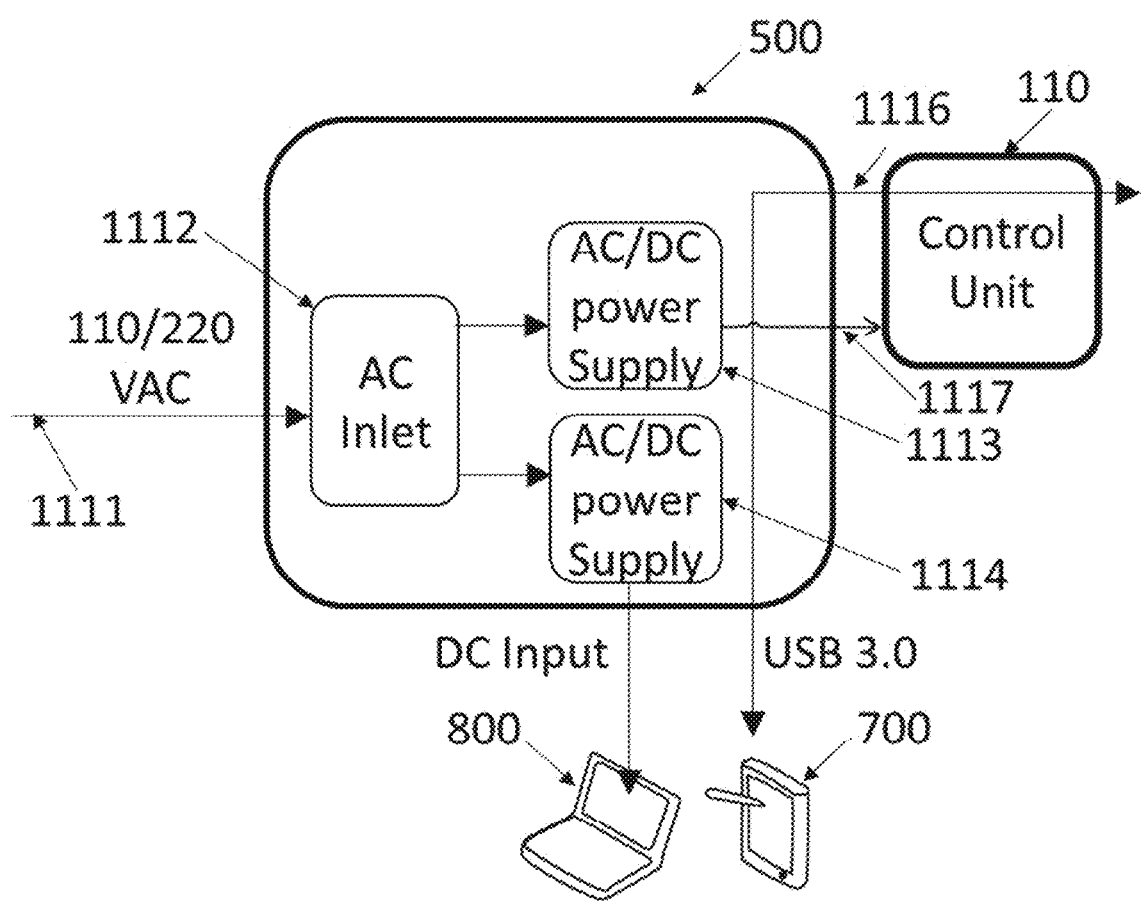
FIG. 23 shows an embodiment of a block diagram of electronics for a base unit.

FIG. 23 shows an embodiment of a block diagram of electronics for a base unit (500). The base unit (500) inputs 110.220 V AC (1112) from a standard AC power supply (1111). The input power is fed to two internal AC/DC power supplies (1113, 1114), configured to supply AC and/or DC power at the voltages and currents needed by other components. One power supply (1113) can supply power, typically DC power (1117), to the control unit (110). The other power supply (1114) can supply DC power to a processor (800) configured for analysis, storage, input and/or display. A display unit (700) is connectable (1116), via the base unit (500) and the control unit (110) to an imaging device (not shown) in a head module (not shown).

Control Module

Figure 24:
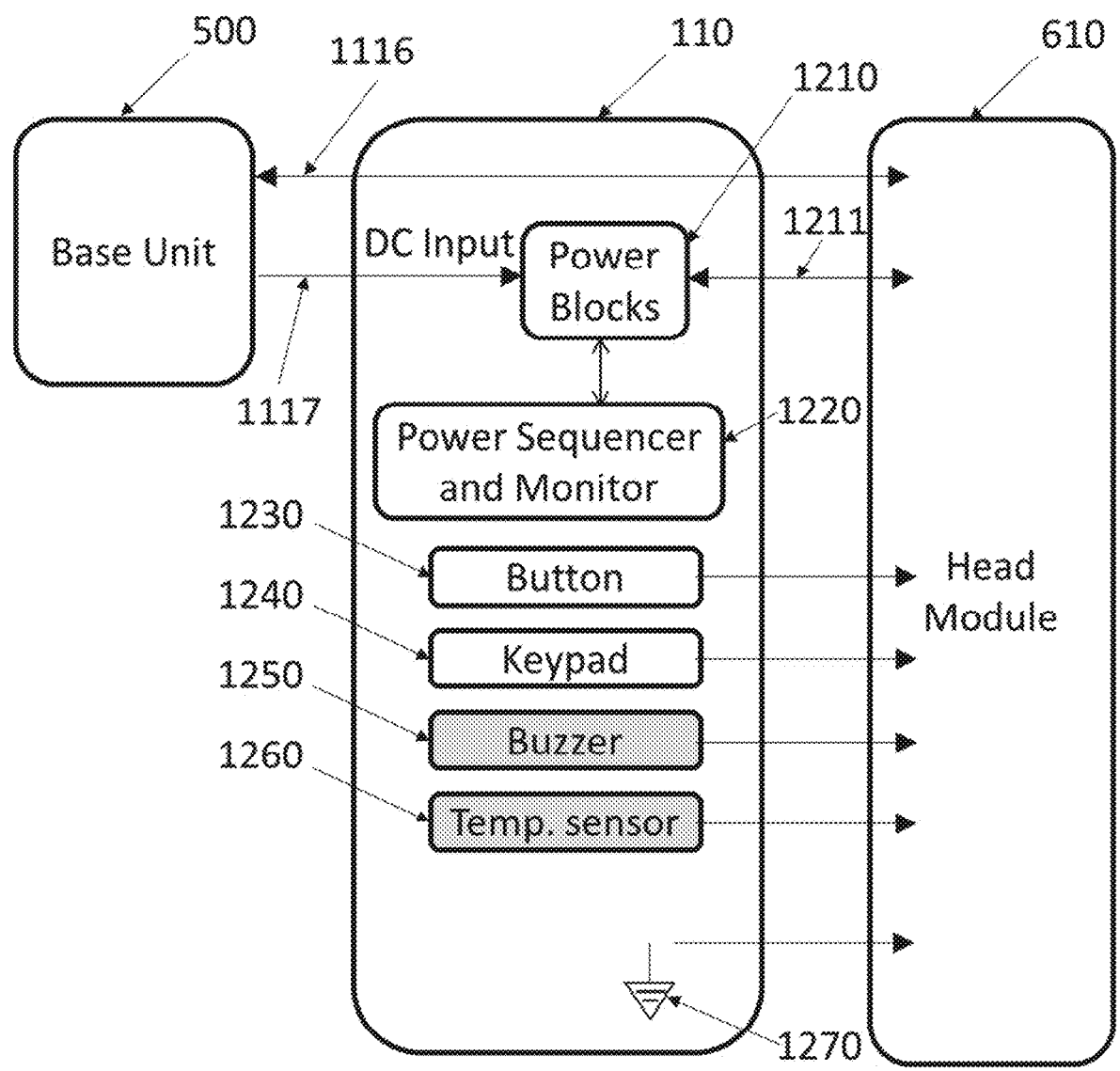
FIG. 24 shows an embodiment of a block diagram of electronics for a control module.

FIG. 24 shows an embodiment of a block diagram of electronics for a control module (110). DC input power can be supplied (1117) to the power blocks (1210) by the base unit (500). The power blocks (1210) can supply power (1211) to a head module (610), which can be any of the head modules disclosed above. The amount of power supplied to the head module (610) and the sequence in which the power is supplied to components within the head module is controlled and monitored by the power sequencer and monitor (1220). A button (1230) controls activation and deactivation of the head module (610). Other control functions are supplied by a keypad (1240). A buzzer (1250) connected to the head module (610) can be activated when a procedure is complete. Temperature is monitored by a temperature sensor (1260). The control module (110) and head module (610) share a common ground (1270). A display unit (700, not shown) is connectable (1116) via the base unit (500) and the control unit (110) to either at least one sensor (not shown) in a head module (610) or to a processor (not shown) to display processed information.

Digital Colposcope Module

Figure 25:
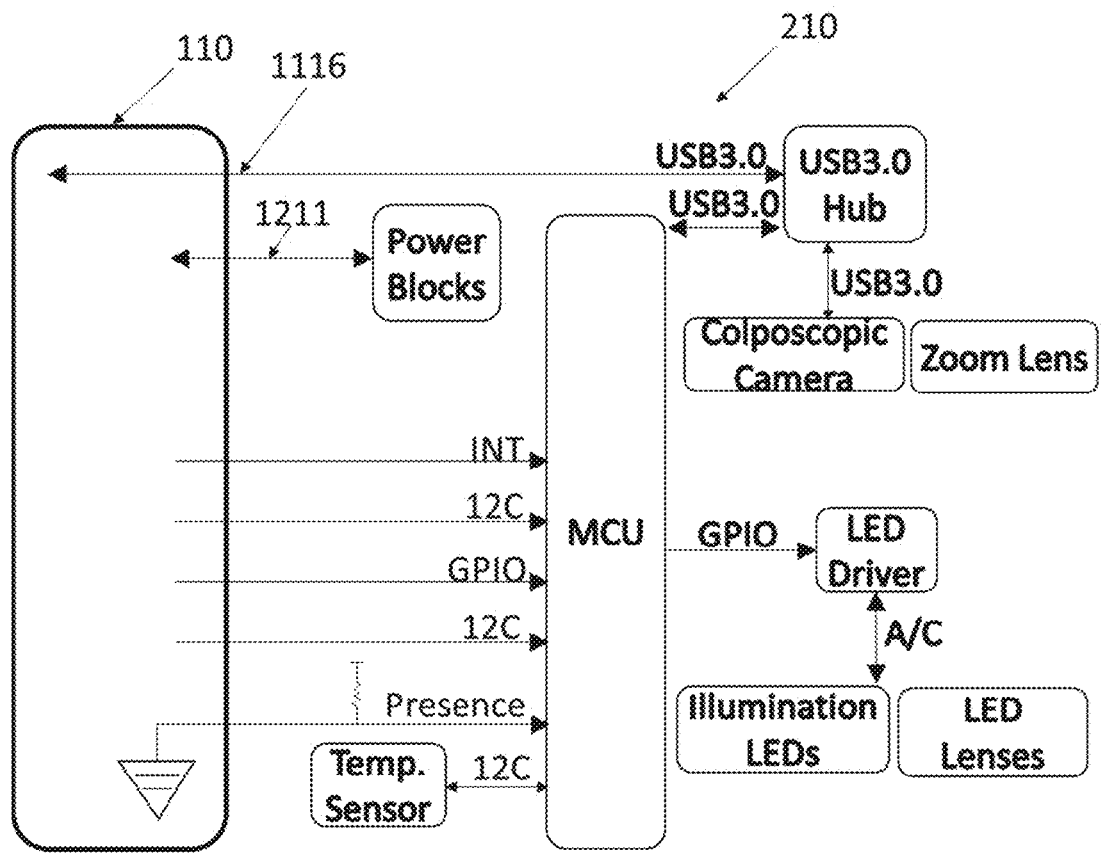
FIG. 25 shows an embodiment of a block diagram of electronics for a digital colposcope module.

FIG. 25 shows an embodiment of a block diagram of electronics for a digital colposcope module (210). A display unit (700, not shown) is connectable (1116) via the base unit (500, not shown) and the control unit (110) to a USB hub, which further connects to a colposcopic camera and zoom lens. The button, keypad buzzer and sensor in the control unit (110) are connected, as described above for the control module, to a main control unit (MCU) in the digital colposcope module (210). The MCU controls and receives input from an LED driver, and the illumination LEDs and LED lenses.

Optical Probe Module

Figure 26:
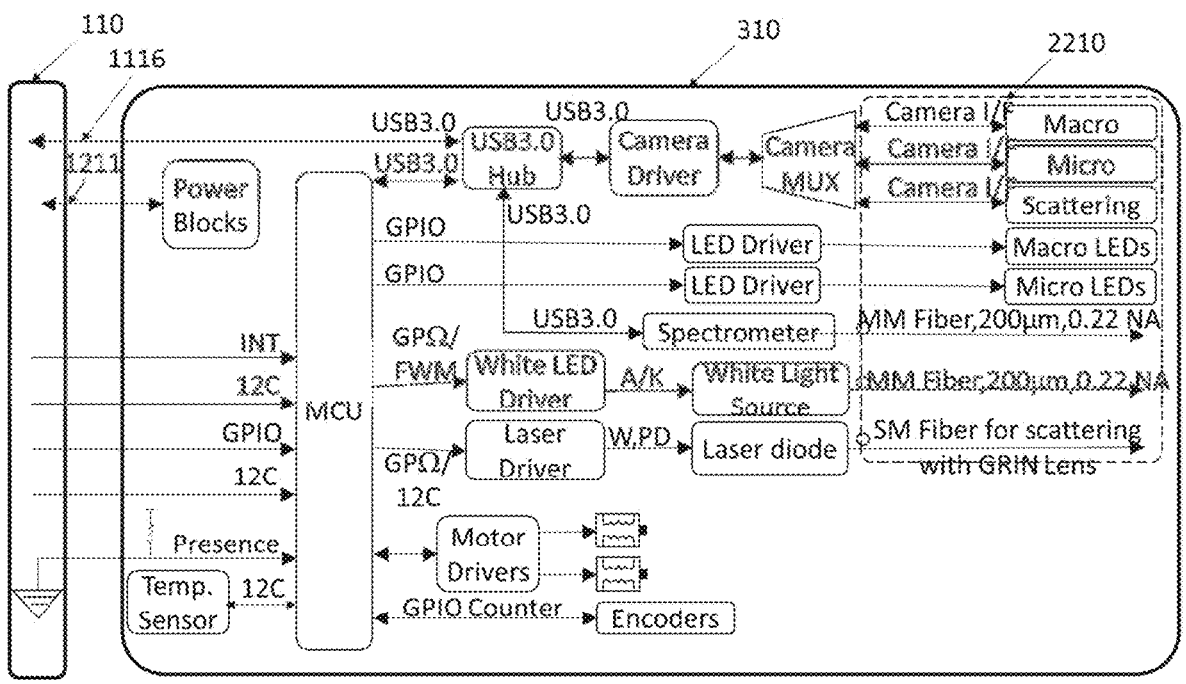
FIG. 26 shows an embodiment of a block diagram of electronics for an optical probe module.

FIG. 26 shows an embodiment of a block diagram of electronics for an optical probe module (310). A display unit (700, not shown) is connectable (1116) via the base unit (500, not shown) and the control unit (110) to a USB hub, as described above for the control module, which further connects to a camera driver which drives the macro camera, the micro camera and the scattering camera in the probe head (2210). The USB hub also connects to a spectrometer, configured to receive light via a 200 μm fiber in the probe head (2210). The button, keypad buzzer and sensor in the control module (110) are connected to a main control unit (MCU). The MCU controls two LED drivers, one for the macro camera and one for the micro camera. The MCU also controls a white LED light source driver and white light source and a laser driver and laser diode. The light passes through the probe head via fibers. In addition, the MCU controls motor drivers and their associated motors to move the probe head and its optics. The MCU also controls and receives data from encoders to locate the position of the probe head and/or the optics and receives data from a temperature sensor, which is returned to the control module.

Example 7—Optical Setup Assessment in Human Normal and Cervical Cancer Xenograft Mouse Model Early preclinical tests were performed using human normal tissue and cancer xenograft mouse model tissue, utilizing the scattering feature and spectroscopic feature set ups to demonstrate the ability to distinguish between abnormal and normal tissues. These tests showed that the optical probe's scattering and spectroscopy components successfully differentiated between the optical signatures of normal versus abnormal tissues in a human cervical cancer tumor-bearing mouse model.

Example 8—Preliminary Ex-vivo Proof of Concept Study on Human Cervical Tissue Following the results from preclinical studies with the tumor-bearing mouse model, a study using excised human tissue was designed in order to further fine-tune the scattering and spectroscopy optical features, and to demonstrate the ability of the spectroscopy and scattering optical set-ups to distinguish between abnormal and normal tissues of resected cone biopsy specimens.

A total of 15 women with a biopsy diagnosis of cervical dysplasia underwent colposcopy following which a loop electro excisional procedure was performed. The conization specimens were marked with normal and abnormal areas according to the clinician's assessment during colposcopy and were scanned with the optical set-ups and the results recorded.

Figure 27:
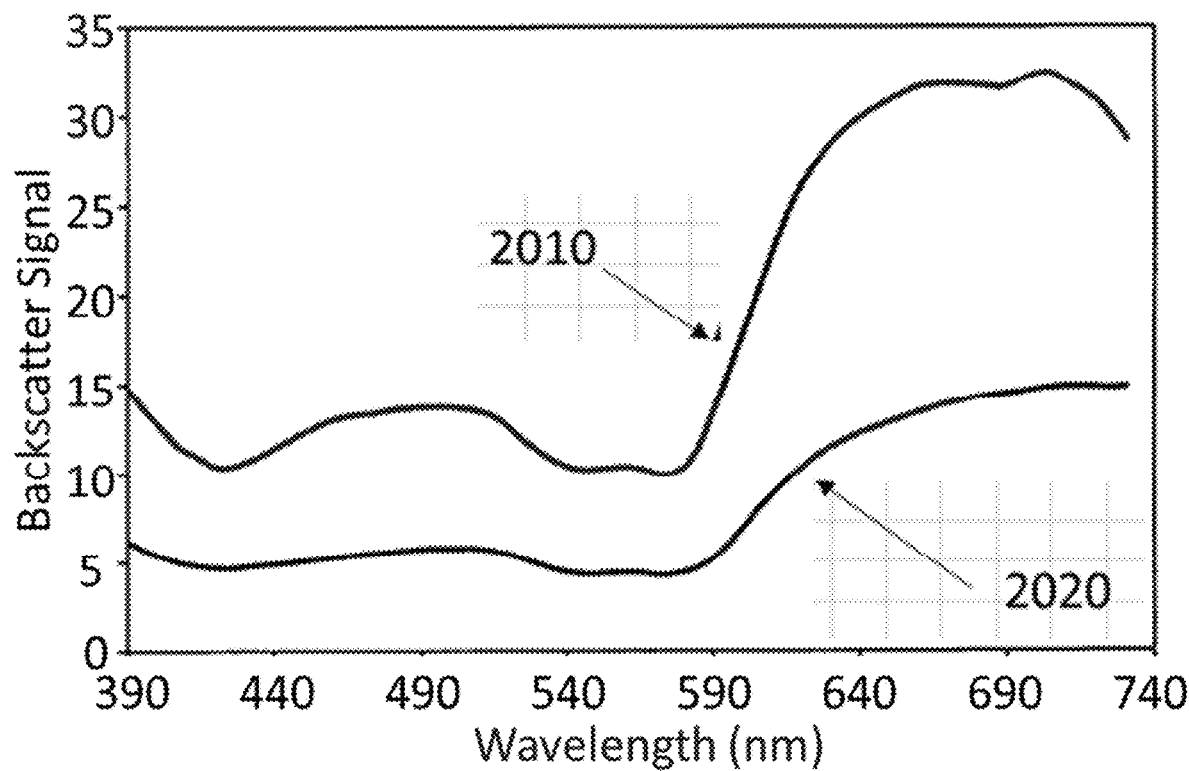
FIG. 27 depicts measured subsurface scattering light spectra from normal and abnormal tissue versus wavelength.

Spectroscopy:

White light was shone onto the tissue samples and measured subsurface scattering spectra at different wavelengths (FIG. 27) were processed by the algorithms disclosed above, enabling the extraction of several parameters to characterize the shapes of the spectra for different wavelengths of light. The cancerous tissue (2020) has a distinctly different spectrum from the normal tissue (2010) at all of the measured wavelengths.

Figure 28:
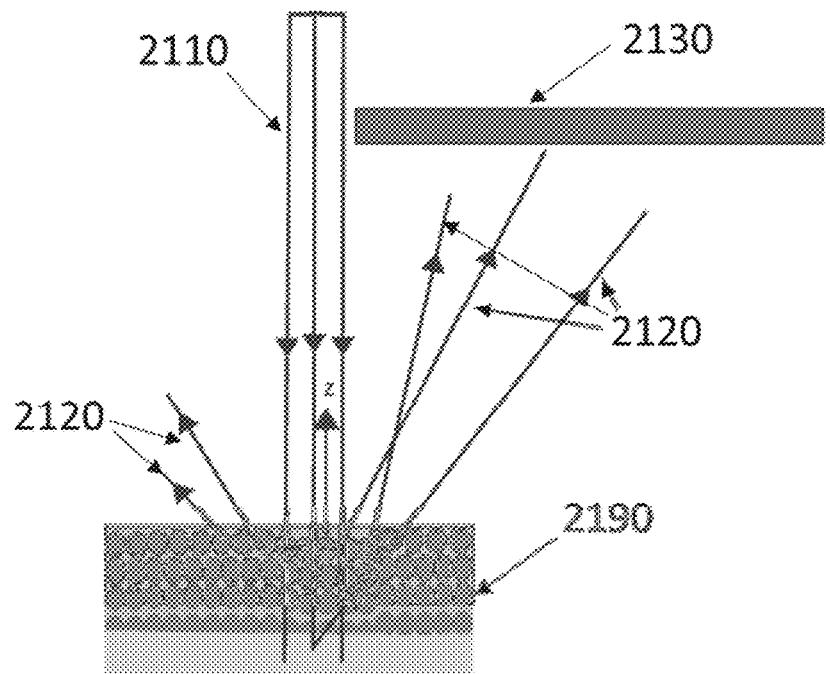
FIG. 28 schematically illustrates a setup for measuring the spatial distribution of light scattered from excised tissue.

Scattering:

To measure the spatial distribution of the scattered light, as shown in FIG. 28, the tested tissue (2190) was illuminated by a narrow monochromatic infrared laser beam (2110). The scattered light (2120) was captured by a complementary metal-oxide-semiconductor (CMOS) detector (2130), which was placed at a fixed distance from the window glass attached to the tested tissue.

The captured CMOS images of all samples and parameters were extracted as was the speckle size and asymmetry in speckle distribution.

The extracted parameters from spectroscopy and scattering were used as the input of the classifier function for assessment of system accuracy vs. clinical examination.

The specimens were then sent for pathological evaluation by a blinded pathologist. Formal colposcopy records and optical probe images were then evaluated and compared with the final pathology report.

Results: Ninety-seven samples were taken forty five samples from 'abnormal areas' and 42 samples from 'normal areas', as defined by the clinician. The pathologist diagnosed 58 samples as dysplastic and 39 samples as normal. Clinician assessment yielded sensitivity of 48% and specificity of 49%.

The optical probe scan predicted 58 sample points as abnormal and 39 points as normal with sensitivity of 90% and specificity of 77%.

The invention claimed is:

1. A device for imaging a cervix comprising:
at least one light source, configured to generate light, said light illuminating tissue in at least a portion of said cervix; and
at least one sensing device selected from the group consisting of an imaging camera, a spectrometer, an intensity sensor and any combination thereof; said at least one sensing device configured to generate at least one signal from at least a portion of light scattered from said illuminated tissue;
a cover separating said at least one light source and said at least one sensing device from said cervix;
wherein said at least one sensing device senses only light scattered from said tissue;
wherein said at least one sensing device is laterally spaced apart from said at least one light source at lateral distance $D_s$, said lateral distance being measurable in a plane parallel to a sensing face of said at least one sensor; said distance $D_s$ is calculated from:

$$D_s = 0.5 \cdot Bd + ta \cdot \tan(Aa) + tg \cdot \tan\left[a\sin\left(\frac{\sin(Aa)}{n}\right)\right],$$

where Bd is diameter of illumination beam, to is distance from said cover to said scattering sensor, tg is thickness of said cover, Aa is angle of light scattered back after reflection by nucleus of cells of tissue in said cervix.

2. The device of claim 1, wherein at least one of the following is true:
a. in use, for said distance $D_s$, light either reflected or scattered from said cover can does not impinge upon any sensing region of said at least one sensing device;
b. said at least one sensing device is configured to generate at least one signal from autofluorescent light generated by said portion of said cervix illuminated by said light;
c. said at least one sensing device is selected from a group consisting of: a camera, a scattering detector, an intensity detector, a spectrometer, and any combination thereof; and
d. said device comprises at least one control module configured to be connectable to at least one power source;
e. said at least one light source and said at least one sensing device comprise a member of a group consisting of: at least one white light source and at least one spectrometer, at least one laser and at least one scattering sensor, at least one laser and at least one intensity sensor, at least one excitation light source and at least one wavelength-sensitive sensor, and any combination thereof;
f. a size of at least a portion of a cervix is determinable automatically by generating a laser beam parallel to and at a predetermined distance from a centerline of said at least one sensing device, imaging said at least a portion of said cervix, measuring, from said image, a distance between said image of said at least a portion of said cervix and a centerline of said at least one sensing device, said distance in said image between said at least a portion of said cervix and said centerline of said at least one sensing device being a spot distance, and determining said size of said at least a portion of said cervix from a ratio of said spot distance and said predetermined distance;
g. at least one sensing device is configured to generate at least one signal from light impinging on said at least one sensing device;
h. said device comprises said at least one changeable head module at least partially reversibly connectable to said at least one control module, said at least one changeable head module configured to image at least a portion of said cervix;
i. said at least one changeable head module comprises at least one first sensing device configured to provide at least one first image at a first resolution of at least a portion of a cervix; and at least one second sensing device configured to provide at least one second image at a second resolution of at least a portion of a cervix.

3. The device of claim 2, wherein at least one of the following is true:
said at least one power source is comprised within a base unit;
said excitation light source is configured to be effective for auto-fluorescence excitation.

4. The device of claim 3, wherein at least one of the following is true:
said at least one changeable head module is selected from a group consisting of: a digital colposcope module, an optical probe module, an endo-cervical endoscope module and any combination thereof;
said at least one control module is configured to provide at least one of a group consisting of activation and movement to said at least one changeable head module;
said at least one of a group consisting of activation and movement of said at least one changeable head module by said control module is selected from a group consisting of: zoom of optical elements in said at least one changeable head module, focus of optical elements in said at least one changeable head module, level of illumination from a light source in said at least one changeable head module, selection of single image or video imaging; acquisition of an image, translation of said at least one changeable head module, rotation of said at least one changeable head module, translation of an optical element within said at least one changeable head module, rotation of an optical element within said at least one changeable head module, and any combination thereof;
upon connection between said at least one control module and said at least one changeable head module a cervical examination device is provided;
said at least one light source is selected from a group consisting of: a white light source, a laser, a near infrared (NIR) light source, a visible light source, a UV light source, and any combination thereof;

said at least one sensing device is selected from a group consisting of: a camera, a scattering detector, an intensity detector, a spectrometer, and any combination thereof; and said at least one changeable head module comprises said at least one light source and said at least one sensing device.

5. The device of claim 4, wherein said camera is selected from a group consisting of: a panoramic camera, a camera for capturing scattering patterns, a close-up camera, a video camera, and any combination thereof.

6. The device of claim 4, wherein said at least one changeable head module is configured to either video image said at least a portion of said cervix or to provide at least one image of said at least a portion of said cervix.

7. The device of claim 3, wherein at least one of the following is true:

said at least one changeable head module comprises an optical fiber connected to a spectrometer;

said at least one control module additionally comprises a timer;

said device comprises at least one processor connectable to said control module;

said device comprises a support unit;

said device comprises at least one motor maneuvering a tip of said endo-cervical endoscope module;

said at least one changeable head module additionally comprises a multifunctional passage for at least one member of a group consisting of: sampling said tissue at at least one suspicious location, administering a medicine into a cervix; and administering a non-medicinal material into a cervix.

8. The device of claim 7, wherein said timer, when connected to said at least one changeable head module, controls a member of a group consisting of: activation of said illumination in said at least one changeable head module, deactivation of said illumination in said at least one changeable head module, activation of translation of said at least one changeable head module, activation of rotation of said at least one changeable head module, activation of translation of an optical element within said at least one changeable head module, activation of rotation of an optical element within said at least one changeable head module, deactivation of translation of said at least one changeable head module, deactivation of rotation of said at least one changeable head module, deactivation of translation of an optical element within said at least one changeable head module, deactivation of rotation of an optical element within said at least one changeable head module, and any combination thereof.

9. The device of claim 7, further comprising an endoscope cover configured to cover at least a portion of said endo-cervical endoscope module.

10. The device of claim 9, wherein at least one of the following is true:

at least a portion of said endoscope cover is transparent in at least the visible and near infrared wavelengths of light;

said endoscope cover is configured to support a tip of said endoscope; and said endoscope cover is a sterile, single use cover.

11. The device of claim 7, wherein said at least one processor comprises software configured to process information generable by said cervical examination device and to generate at least one result from said processed information.

12. The device of claim 11, wherein at least one of the following is true:

said software additionally comprises at least one learning algorithm to improve quality and accuracy of said at least one value indicating probability of presence of abnormal tissue at said at least one location;

said at least one result comprises at least one location in a cervix and, for each said at least one location, at least one value indicating probability of presence of abnormal tissue at said at least one location.

13. The device of claim 7, wherein at least one of the following is true:

said support unit is configured to stably support said base unit;

said support unit is configured to stably support said at least one changeable head module;

said support unit is configured to stably support said at least one processor;

said support unit is configured to stably support at least one said display;

said device comprises an optical probe cover configured to cover said optical probe module.

14. The device of claim 13, wherein at least one of the following is true:

said optical probe cover is a sterile, single-use cover;

at least a portion of said optical probe cover is transparent in at least the visible and near infrared wavelengths of light.

15. The device of claim 1, wherein at least one of the following is true:

a difference between normal and abnormal cells is determinable by at least one difference between normal cell backscattered intensity and abnormal cell backscattered intensity at at least one angle relative to the direction of the incident light;

a probability of abnormal cells at said at at least one location is generable from combining a plurality of members of a group consisting of: a result generated from backscattering data, a result generated from backscattering intensity data, a result generated from spectrometer data, a result generated from autofluorescence data and any combination thereof;

said at least one probability value indicating probability of presence of abnormal tissue is generable automatically.

16. The device of claim 15, at least one of the following is true:

said device is configured to, for at least one location in a cervix, generate said at least one probability value at said at least one location;

said device comprises at least one display for displaying said at least one result; and said device comprises at least one database for storing at least one said result.

17. The device of claim 2, wherein said at least one sensing device is configured to acquire at least two images of said at least a portion of said cervix, each of said at least two images acquired at a different time, and said at least one processor is configured to measure, for each of said at least two images, said spot distance.

18. The device of claim 17, wherein, from a difference between a spot difference for a first of said at least two images and a spot distance for a second of said at least two images, movement of said cervix can be determined.

19. The device of claim 2, wherein at least one of the following is true:

said at least one processor is further configured to analyze said at least one signal generated by said at least one sensing device;

said at least one signal is selected from a group consisting of: intensity of light as a function of wavelength; intensity of light as a function of spatial distribution of laser light scattered by tissue in said cervix, said portion of said cervix and said at least one sensing device; intensity of light as a function of position in an image acquired by said imaging device; color of reflected light; color of reflected light as a function of position in an image acquired by said imaging device; change in color of light between pixels in an image; and any combination thereof.

20. The device of claim 19, wherein at least one of the following is true:
   said at least one processor is further configured to:
      i. determine at least two substantially different parameters, each of which defines at least one property of said cervix;
      ii. analyze said at least one signal, based on said at least two parameters, to determine and distinguish normal tissue from abnormal tissue within said cervix;
   said at least two parameters are detectable by the same sensor, or by different sensors.

21. The device of claim 19, wherein said property of said cervix is selected from a group consisting of: cell nucleus size, amount of fibrous stroma collagen in a cell, amount of collagen in the stroma, texture of tissue, color of tissue, blood vessel density, amount of keratin in tissue, spectrum of autofluorescence of cells, and any combination thereof.

22. The device of claim 2, wherein at least one of the following is true:
   said second resolution is higher than said first resolution;
   said at least one first image and said at least one second image at least partially overlap;
   said at least one processor is in communication with said at least one first sensing device and said at least one second sensing device, said at least one processor is configured to image process said at least one first image and said at least one second image to generate a combined image;
   said at least one processor is in communication with each said at least one sensing device, said at least one processor is configured to analyze, for each said at least one sensing device, said at least one signal, determine at least one parameter which defines at least one property of said cervix, analyze said at least one parameter to define and distinguish normal tissue and abnormal tissue within said cervix as a function of location within said cervix and, if there exists at least one area of abnormal tissue, to determine a location in said cervix of each said at least one area of abnormal tissue.

23. The device of claim 22, wherein at least one of the following is true:
   an image processing comprises at least one action selected from a group consisting of removing distortion from said at least one first image and said at least one second image; registering said at least one first image and said at least one second image; stitching together said at least one first image and said at least one second image; and any combination thereof;
   said combined image is a panoramic view of at least a portion of said cervix;
   said at least one processor is further configured, if there exists said at least one area of abnormal tissue, to mark at said location on said image each said at least one area of said abnormal tissue;
   said at least one processor is additionally configured to execute a learning algorithm to improve at least one of a group consisting of quality and accuracy of determination of probability of normal tissue and abnormal tissue;
   said at least one processor is additionally configured to generate a map indicating the probability of normal tissue and abnormal tissue as a function of location in the image of at least a portion of a cervix.

24. The device of claim 23, wherein at least a portion of said marked image is displayable.

25. The device of claim 24, wherein at least a portion of said map is displayable.

* * * * *